(12) United States Patent
Bekki et al.

(10) Patent No.: US 8,501,492 B2
(45) Date of Patent: Aug. 6, 2013

(54) MEASUREMENT DEVICE USED FOR SPECIFICALLY DETECTING SUBSTANCE TO BE EXAMINED USING PHOTOCURRENT, SENSOR UNIT USED FOR SAME, AND METHOD FOR SPECIFICALLY DETECTING SUBSTANCE TO BE EXAMINED USING PHOTOCURRENT

(75) Inventors: Makoto Bekki, Fukuoka (JP); Shuji Sonezaki, Fukuoka (JP)

(73) Assignee: Toto Ltd., Fukuoka (JP)

( * ) Notice: Subject to any disclaimer, the term of this patent is extended or adjusted under 35 U.S.C. 154(b) by 0 days.

(21) Appl. No.: 13/256,713

(22) PCT Filed: Mar. 18, 2010

(86) PCT No.: PCT/JP2010/054672
§ 371 (c)(1),
(2), (4) Date: Nov. 22, 2011

(87) PCT Pub. No.: WO2010/107088
PCT Pub. Date: Sep. 23, 2010

(65) Prior Publication Data
US 2012/0100627 A1    Apr. 26, 2012

(30) Foreign Application Priority Data
Mar. 18, 2009 (JP) .................................. 2009-065850

(51) Int. Cl.
*G01N 27/00* (2006.01)
*G01N 30/96* (2006.01)
*G01N 30/00* (2006.01)

(52) U.S. Cl.
USPC ............... 436/149; 422/69; 422/68.1; 422/50

(58) Field of Classification Search
USPC ............................. 422/69, 68.1, 50; 436/149
See application file for complete search history.

(56) References Cited

U.S. PATENT DOCUMENTS

| | | |
|---|---|---|
| 5,084,365 A | 1/1992 | Gratzel et al. |
| 5,776,672 A | 7/1998 | Hashimoto et al. |
| 6,491,871 B1 | 12/2002 | Fodor et al. |
| 2008/0318232 A1 | 12/2008 | Gao |

FOREIGN PATENT DOCUMENTS

| | | |
|---|---|---|
| JP | 1-220380 A | 9/1989 |
| JP | 07-107999 A | 4/1995 |
| JP | 2573443 B2 | 1/1997 |
| JP | 11-315095 A | 11/1999 |
| JP | 2000-083647 A | 3/2000 |
| JP | 2002-181777 A | 6/2002 |
| JP | 2006-119111 A | 5/2006 |
| JP | 2006-250695 A | 9/2006 |
| JP | 2008-545136 A | 12/2008 |
| WO | 2005/093418 A1 | 10/2005 |

OTHER PUBLICATIONS

Yoshio Ishimori, "DNA Chips", Hyomen Kagaku (Surface Science), vol. 24, No. 11, p. 671-676, 2003, Corporate Research and Development Center, Toshiba Corporation, Kanagawa 212-8582 Japan.
Nakamura et al., "Koden Henkan Niyoru Atarashii DNA Nihonsa Kenshutu Hoho (Novel method for detecting DNA duplex by photoelectric conversion)," Proceedings of Meeting of the Chemical Society of Japan, vol. 81st. No. 1(2002) p. 947.

*Primary Examiner* — Christine T Mui
(74) *Attorney, Agent, or Firm* — Carrier Blackman & Associates P.C.; William D. Blackman; Joseph P. Carrier

(57) ABSTRACT

In utilizing photocurrent generated in the photoexcitation of a dye in specific detection of an analyte, highly accurate detection can be realized by discharging charged current generated in the formation of a sensor unit and, in the detection of photocurrent of a plurality of detection spots provided on a working electrode, discharging photocurrent which is derived from a detection spot subjected to the latest photocurrent measurement and becomes noise current. The present invention provides a measuring apparatus comprising a sensor unit comprising a working electrode, a counter electrode, and an electrolyte-containing substance, a single or plurality of light sources that apply light to the working electrode, an XY moving device provided when the light source is moved relatively in an XY direction relative to the working electrode, an ammeter that measures current which flows across the working electrode and the counter electrode, and a discharge device that discharges charged current and photocurrent derived from a detection spot subjected to the latest photocurrent measurement. The specific detection method using the measuring apparatus is carried out by controlling the timing of light irradiation and the timing of connection to the ammeter and the discharge device.

17 Claims, 18 Drawing Sheets

(a)

(b)

MEASUREMENT DEVICE USED FOR SPECIFICALLY DETECTING SUBSTANCE TO BE EXAMINED USING PHOTOCURRENT, SENSOR UNIT USED FOR SAME, AND METHOD FOR SPECIFICALLY DETECTING SUBSTANCE TO BE EXAMINED USING PHOTOCURRENT

TECHNICAL FIELD

The present invention relates to a method for specifically detecting analytes having specific bindability such as nucleic acids, exogenous endocrine disrupting chemicals, and antigens; and a sensor unit; and a measuring apparatus for use in the same.

BACKGROUND ART

Genetic diagnostics for use in the analysis of DNA in biological samples are promising new preventive and diagnostic methods for various diseases. The following techniques have been proposed as techniques that can analyze DNA in a simple and accurate manner.

A method for analyzing DNA is known that comprises the steps of hybridizing an analyte DNA with a DNA probe that has a base sequence complementary to the analyte DNA and is labeled with a fluorescent substance, and detecting a fluorescent signal generated upon the hybridization (see, for example, JP H7 (1995)-107999A (PLT 1) and JP H11 (1999)-315095A (PLT 2)). In this method, the formation of double stranded DNA by the hybridization is detected by fluorescence of a dye.

A method is also known that comprises hybridizing a gene sample modified to a single strand with a single stranded nucleic acid probe complementary thereto, then adding a double stranded recognition substance such as an intercalator, and performing electrochemical detection (see, for example, JP 2573443B (PLT 3) and Hyomen Kagaku (Surface Science) Vol. 24, No. 11. pp. 671-676, 2003 (NPL 1)).

On the other hand, in recent years, damage to genital systems, nervous systems and the like by exogenous endocrine disrupting chemicals (environmental hormones) including dioxins is recognized as social problems. At the present time, various methods are used to detect exogenous endocrine disrupting toxicity. Such chemicals exhibit toxicity at a very low concentration on a level of approximately 10 ppt. Accordingly, the development of a method for detecting exogenous endocrine disrupting chemicals in a low concentration range has been desired.

In particular, exogenous endocrine disrupting chemicals are bound to target DNA through a protein such as a receptor and so that it influences the expression of the DNA, whereby toxicity is produced. That is, the exogenous endocrine disrupting chemicals are bound indirectly to DNA through a protein such as a receptor rather than direct binding to DNA. Accordingly, in conventional methods such as pre-screening using DNA bindability, the evaluation of the binding is not easy.

Solar batteries are known for generating electric energy from light using sensitizing dyes (see, for example, JP H1 (1989)-220380A (PLT 4)). Solar batteries comprise a polycrystalline metal oxide semiconductor and a layer of a sensitizing dye provided in a wide range of the surface area of the semiconductor.

Further, a proposal of utilizing photocurrent generated by the photoexcitation of dyes in the detection of analytes (biological molecules such as DNAs and proteins) has been made as an attempt to apply the properties of such solar batteries in biochemical analyses (see, for example, JP 2002-181777A (PLT 5)). An improvement in measurement accuracy has been still demanded in methods for detecting analytes utilizing photocurrent generated by the photoexcitation of such dyes. As long as the present inventors know, specifying the cause of the so-called noise current and eliminating an influence of the noise current with high efficiency have been demanded.

A gene detection apparatus for determining the presence of a target gene to be detected is also known. In the use of the gene detection apparatus, a single stranded nucleic acid probe having a base sequence complementary to the target gene is immobilized on a surface of an electrode, the probe is reacted with an analyte containing a gene modified to a single strand, a double stranded recognition material is then bound to the nucleic acid probe hybridized with the gene, and the bound product is detected by electrochemical measurement to determine the presence of the target gene (see, for example, JP 2000-83647A (PLT 6)). The electrochemical measurement is carried out by immersing a working electrode and a counter electrode in an electrolysis solution and measuring oxidation current by linear sweep voltammetry. This method can realize the detection of an analyte with high accuracy. In this case, the spot for capturing the analyte in the working electrode should be single. Accordingly, a method that can realize highly efficient measurement of a plurality of samples has been still demanded.

CITATION LIST

Patent Literature

[PLT 1] JP H7 (1995)-107999A
[PLT 2] JP H11 (1999)-315095A
[PLT 3] JP 2573443B
[PLT 4] JP H1 (1989)-220380A
[PLT 5] JP 2002-181777A
[PLT 6] JP 2000-83647A

Non Patent Literature

[NPL 1] Hyomen Kagaku (Surface Science) Vol. 24, No. 11. pp. 671-676, 2003

SUMMARY OF THE INVENTION

Technical Problem

The present inventors have now found that, in a method for specifically detecting an analyte utilizing photocurrent generated by the photoexcitation of a dye, the analyte can be efficiently detected with high accuracy by discharging current generated when an electrolyte-containing substance is brought into contact with a working electrode and a counter electrode. The present inventors have further found that the analyte can be detected more efficiently in a shorter time with higher accuracy by discharging current generated at a detection site subjected to the latest measurement when, in a plurality of sites in an identical working electrode, an analyte is captured and an analyte is specifically detected utilizing photocurrent generated by photoexcitation of a dye. The present invention has been made based on such finding.

Solution to Problem

Accordingly, an object of the present invention is to provide a measuring apparatus that is adapted for use in specific detection of an analyte using photocurrent and can efficiently detect an analyte with high accuracy, and to provide a method for specifically detecting an analyte using photocurrent.

According to the present invention, there is provided a measuring apparatus for specifically detecting an analyte using photocurrent generated by photoexcitation of a sensitizing dye, the measuring apparatus comprising: a sensor unit comprising a working electrode, a counter electrode, and an electrolyte-containing substance; a single or plurality of light sources that apply light to the working electrode; an ammeter that measures current which flows across the working electrode and the counter electrode; a discharge device that discharges charged current and photocurrent derived from a detection spot subjected to the latest photocurrent measurement; and a switching device that connects the sensor unit to the ammeter or the discharge device, the specific detection of the analyte being carried out while controlling timing of light irradiation and timing of connection to the ammeter and the discharge device.

In a preferred embodiment of the measuring apparatus according to the present invention, the measuring apparatus is controlled so that, when the working electrode and the counter electrode have been brought into contact with the electrolyte-containing substance, the sensor unit is connected to the discharge device to discharge charged current generated in the formation of the sensor unit, the sensor unit is connected to the ammeter after the discharge of the charged current, and a single or plurality of detection spots formed on the working electrode are successively irradiated with light to detect photocurrent derived from the sensitizing dye bound to the detection spot.

In a preferred embodiment of the measuring apparatus according to the present invention, the measuring apparatus is controlled so that, in the detection of photocurrent in a plurality of detection spots, after the detection of photocurrent in one detection spot, the sensor unit connected to the discharge device to discharge photocurrent derived from the detection spot subjected to the latest photocurrent measurement, and the sensor unit is again connected to the ammeter, followed by irradiation of the detection spot with light to detect photocurrent derived from the sensitizing dye bound to the detection spot.

According to the present invention, there is provided a method for specifically detecting an analyte, the method comprising: providing a working electrode having a single or a plurality of detection spots with a probe substance specifically bindable directly or indirectly to the analyte being supported on a surface thereof; providing a counter electrode; bringing a sample solution possibly containing the analyte into contact with the working electrode to bind the analyte to the working electrode, a sensitizing dye, when the analyte has been bound to the probe substance, being also immobilized onto the working electrode; and then irradiating the working electrode with light, detecting sensitizing dye-derived photocurrent, which flows across the working electrode and the counter electrode, to detect the presence of the analyte, wherein charged current generated upon the contact of the working electrode and the counter electrode with an electrolyte-containing substance is discharged and after the discharge of the charged current, the single or plurality of detection spots formed on the working electrode are successively irradiated with light, and photocurrent derived from the dye bound to the detection spots is detected.

In a preferred embodiment of the method according to the present invention, when photocurrent for the plurality of detection spots is detected, after the detection of photocurrent for one detection spot, photocurrent derived from the detection spot is discharged, and another detection spot is irradiated with light, followed by the detection of photocurrent derived from the sensitizing dye bound to the detection spot.

Advantageous Effects of the Invention

According to the present invention, the discharge of charged current and photocurrent derived from a detection spot subjected to the latest measurement of photocurrent, which are a noise, can improve detection accuracy in specific detection of an analyte and, at the same time, can significantly shorten the detection time.

DESCRIPTION OF EMBODIMENTS

Measuring Apparatus and Specific Detection Method

Figure 1:
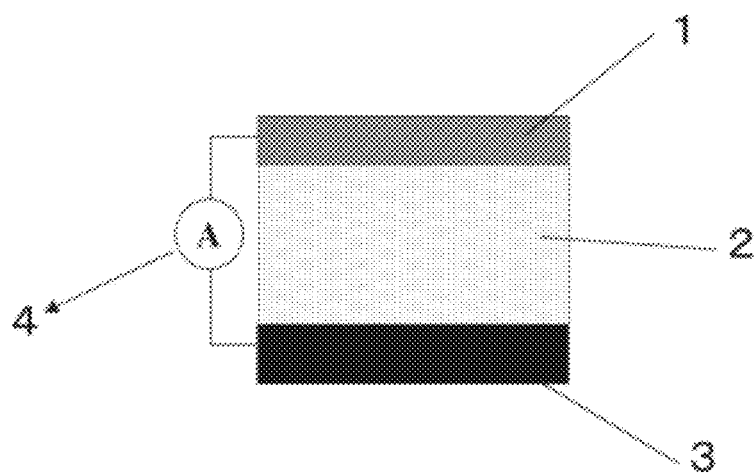
FIG. 1 is a diagram showing one example of a sensor cell in the detection of photocurrent in the present invention.
Figure 2:
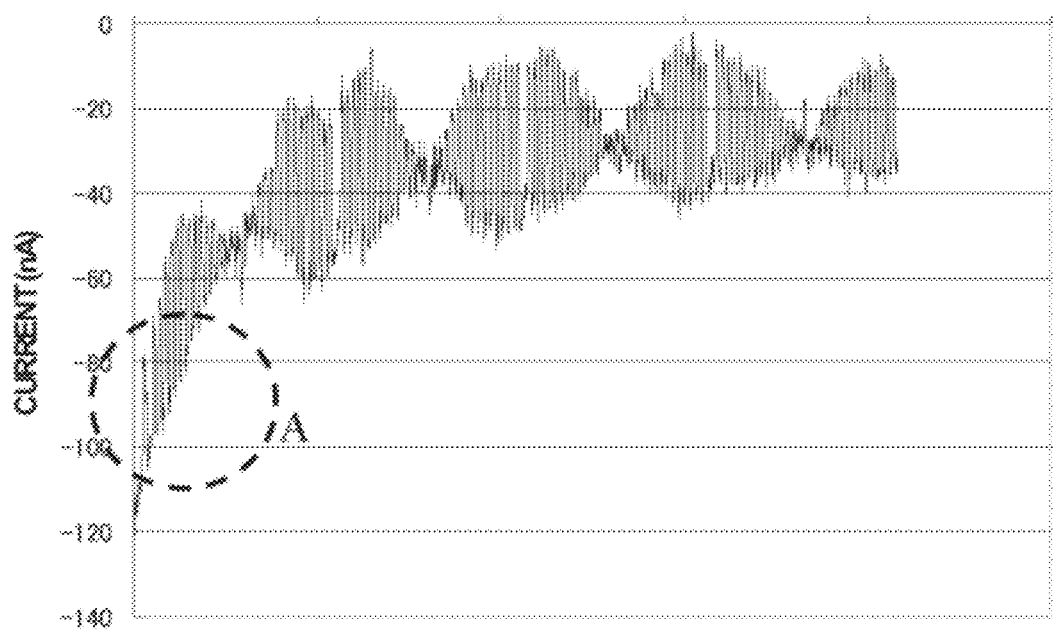
FIG. 2 is a graph showing one example of charged current generated in sensor unit formation.

At the outset, basic features of the apparatus and detection method according to the present invention will be described with reference to the accompanying drawings. In utilizing photocurrent generated by the photoexcitation of a dye in specific detection of an analyte, as shown in FIG. 1, an electrolyte-containing substance is filled into between a working electrode and a counter electrode. The electrolyte is a substance that can function as a reducing agent (an electron donating agent) for donating electrons to a dye excited by photoirradiation. When the electrolyte was filled, a difference in potential occurs between the working electrode and the counter electrode, and, in an early stage of the detection of photocurrent, charged current as shown in FIG. 2A occurs. When the influence of the charged current which is a nose is large, the accuracy of the specific detection of the analyte is disadvantageously lowered. The present invention is characterized in that the charged current is discharged before the measurement of photocurrent. The detection of photocurrent only after the charged current is lowered to render base current stable is considered as means effective for avoiding the problem of the charged current. According to the present invention, such waiting time is not necessary, and the measurement can be immediately carried out with high accuracy.

Figure 3:
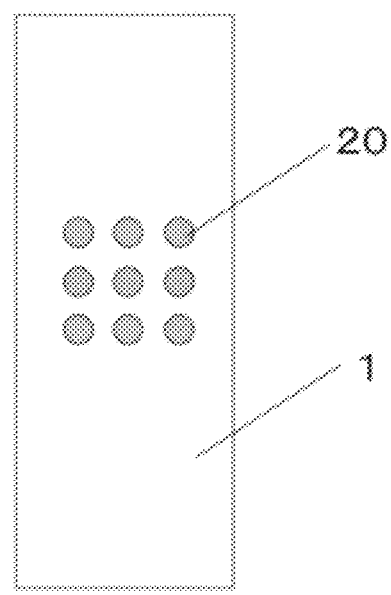
FIG. 3 is a diagram showing one example of a layout of a working electrode with a plurality of detection spots provided therein.
Figure 4:
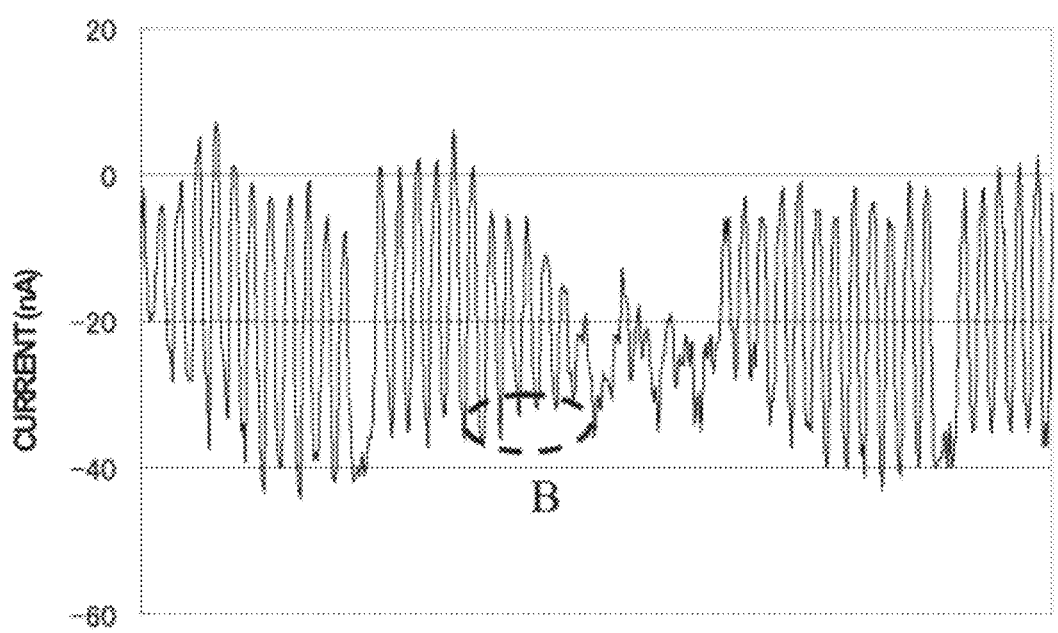
FIG. 4 is a graph showing noise current derived from a detection spot subjected to the latest measurement of photocurrent.

Further, the present invention is characterized in that, as shown in FIG. 3, when a plurality of detection spots 20 are provided on a working electrode 1 and are successively irradiated with light to detect photocurrent, photocurrent derived from a detection spot subjected to the latest measurement of photocurrent is discharged. Highly accurate detection is impossible without discharging the current (see FIG. 4B). The detection of photocurrent after waiting for a satisfactory period of time in such a state that the spot is not irradiated with light is considered as means effective for avoiding the problem. The present invention, however, is very advantageous in that a plurality of detection spots can be measured in a short time.

Figure 5:
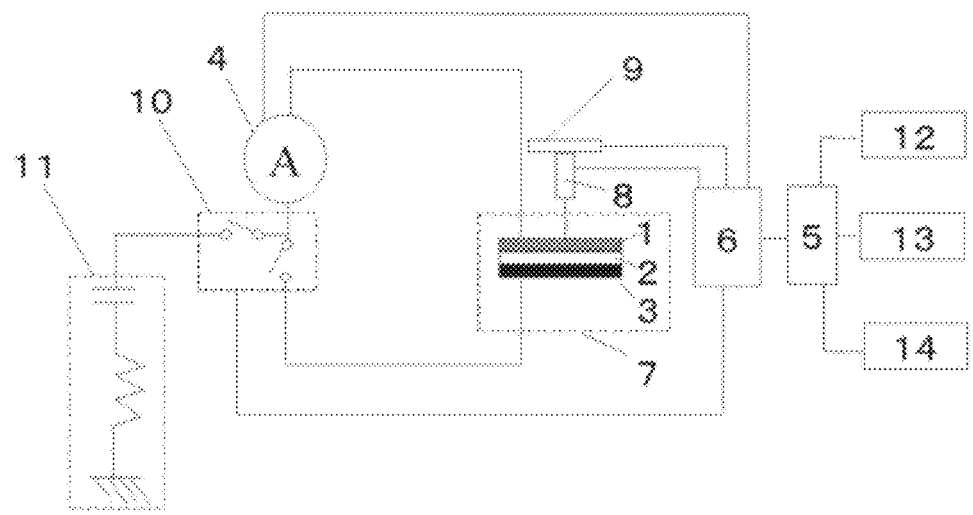
FIG. 5 is a conceptual diagram showing a basic construction of a measuring apparatus that uses an electrolyte-containing sheet and comprises a light source installed in an XY moving device.
Figure 10:
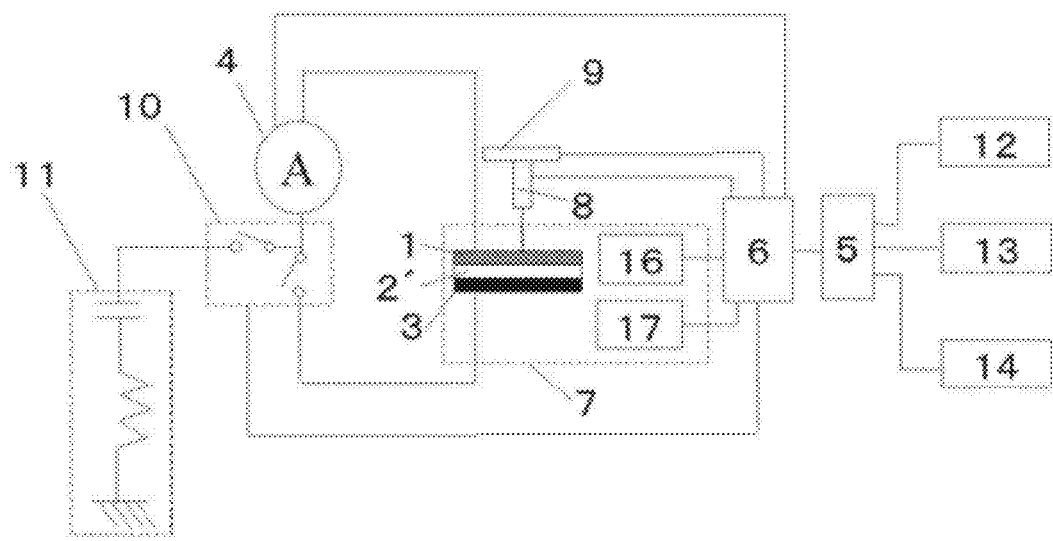
FIG. 10 is a conceptual diagram showing a basic construction of a measuring apparatus using an electrolysis solution.

The measuring apparatus according to the present invention will be described in more detail with reference to the accompanying drawings. FIGS. 5 to 10 are diagrams each showing an example of a measuring apparatus for use in specific detection of an analyte using photocurrent generated by photoexcitation of a sensitizing dye. FIGS. 5 to 9 show examples of the measuring apparatus using an electrolyte-containing sheet as an electrolyte-containing substance, and FIG. 10 shows an example of the measuring apparatus using an electrolysis solution as an electrolyte-containing substance. FIG. 5 shows a construction of an apparatus using an electrolyte-containing sheet 2 as an electrolyte-containing substance. The apparatus comprises: a sensor unit 7 comprising a working electrode 1, an electrolyte-containing sheet 2, and a counter electrode 3; an ammeter 4 that measures current which flows across the working electrode 1 and the counter electrode 3; a light source 8; an XY moving device 9 that moves the light source 8 in an XY direction relative to the working electrode 1; a discharge device 11 that discharges charged current and photocurrent derived from a detection spot subjected to the latest measurement of photocurrent; and a switching device 10 that connects the sensor unit 7 to the discharge device 11 or the ammeter 4. The apparatus further comprises a computer 5 that controls the light source 8, the XY moving device 9, the ammeter 4, and the switching device 10 and receives current signals from the ammeter 4 through an interface board 6. The computer 5 comprises a control computation means that determines at least one of the presence, the type, and the concentration of the analyte based on the electric signal. The measuring apparatus may further comprise a display device 13 that displays the results obtained by the control computation means. The measuring apparatus may further comprise an input device 12 through which conditions for the measurement are input. The measuring apparatus may further comprise a storage device 14 that stores electric signals obtained from the ammeter, the results obtained by the control computation means, and conditions for the measurement. The computer 5 may be an externally mounted PC. Alternatively, a microcomputer may be incorporated in the measuring apparatus. The input device 12, the display device 13, and the storage device 14 may also be incorporated in the measuring apparatus. The functions of the input device 12, the display device 13, and the storage device 14 may be properly divided into those in the microcomputer incorporated in the apparatus and those in the externally mounted PC.

Figure 11:
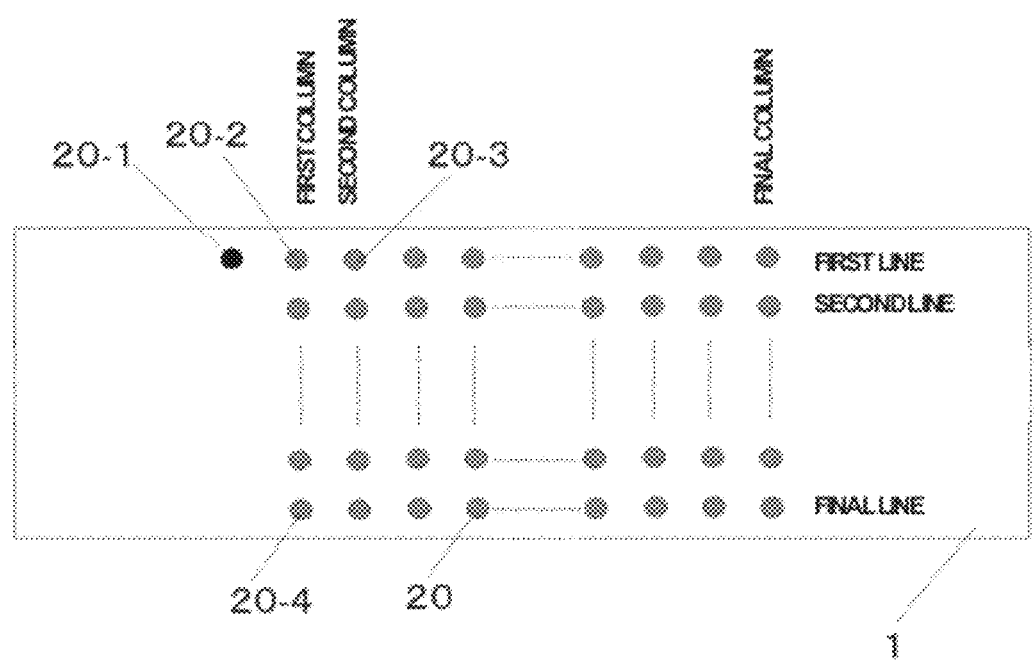
FIG. 11 is a diagram showing one example of a layout of a working electrode with a reference point and a plurality of detection spots provided thereon.

FIG. 11 shows an example of a layout of detection spots 20 provided on a working electrode 1. In the layout of detection spots shown in FIG. 11, the order of irradiation of detection spots with light is such that a reference point 20-1 is irradiated with light to obtain a current value which is a reference, and detection spots from a spot 20-2 in the first column of the first line to a final spot 20-4 in the first column are successively irradiated with light to obtain current.

Figure 12:
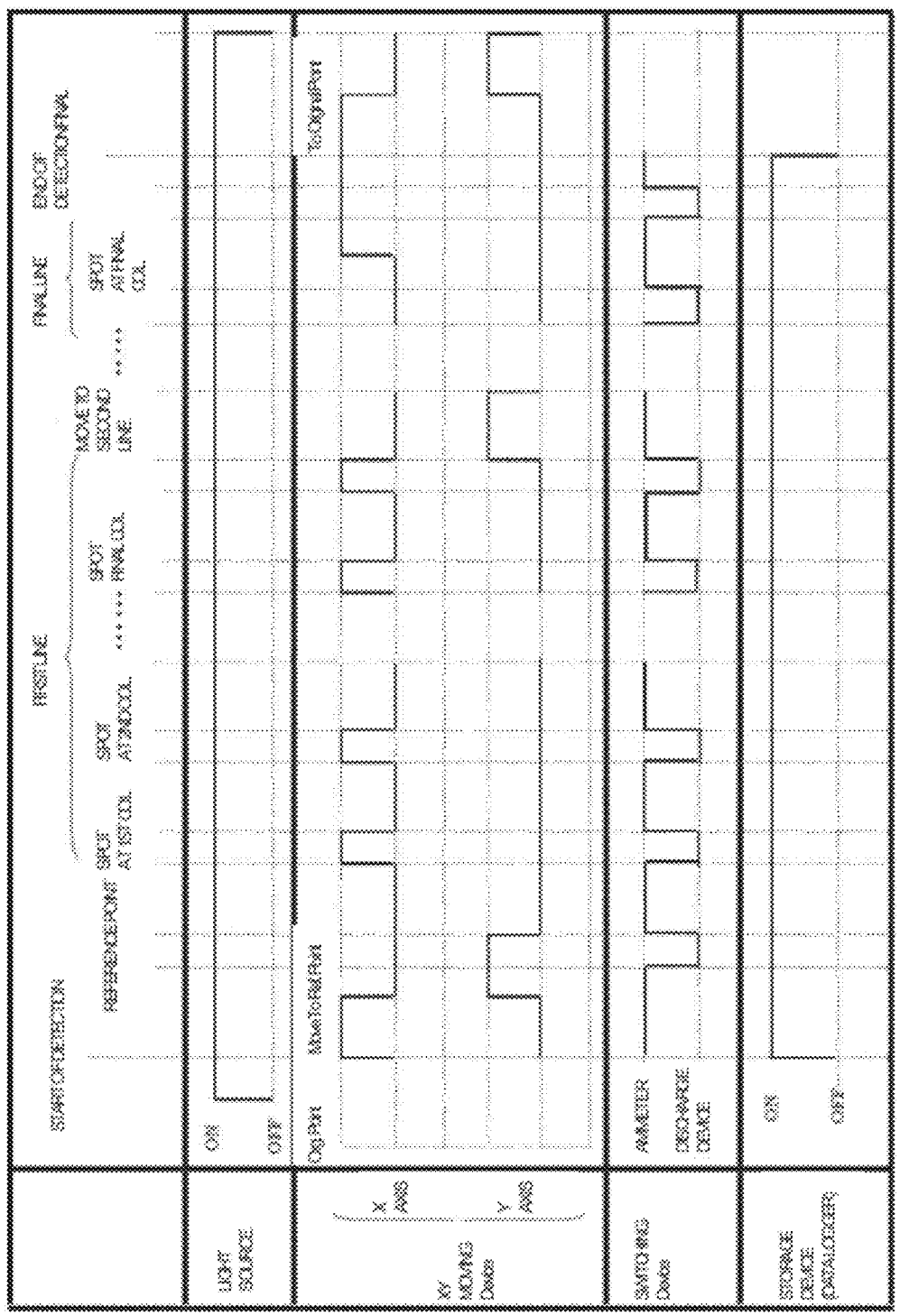
FIG. 12 is a timing chart in the detection of current in a working electrode with detection spots provided in the layout shown in FIG. 11 by the measuring apparatus shown in FIG. 5.

FIG. 12 shows a timing chart in the detection of current in a working electrode with detection spots provided in the layout shown in FIG. 11 by the measuring apparatus shown in FIG. 5. At the outset, a sensor unit 7 is connected to an ammeter 4. A light source 8 is turned on for lighting, and a storage device 14 is started that stores current, which flows across the working electrode 1 and the counter electrode 3, until the detection is completed. Thereafter, the sensor unit 7 is connected to a discharge device 11 by a switching device 10 to discharge charged current generated in the formation of the sensor unit 7. Thereafter, the sensor unit 7 is again connected to the ammeter 4. The light source 8 is moved by an XY moving device 9 to a point where the reference point 20-1 is irradiated with light, and current derived from the reference point 20-1 is generated. The current is obtained at the reference point to confirm the reproducibility among working electrodes. Accordingly, it is desired that, even when substrates are different from each other in layout or the type of solution in spots, the substrates are identical to each other in the type of solution and concentration of the solution in spot at the reference point. However, it is needless to say that, even when the reference point is not provided, current at the detection spot provided on the working electrode can be detected.

Before the light source 8 is moved by the XY moving device 9 to a point where a spot 20-2 at the first column of the first line can be irradiated with light after the storage of a current value derived from the reference point in the storage device 14, the sensor unit 7 is connected to the discharge device 11 by the switching device 10 to discharge the reference point-derived charged current in the sensor unit 7 and the sensor unit 7 is then again connected to the ammeter 4 by the switching device 10. Thereafter, the spot 20-2 at the first column of the first line is irradiated with light, and a current value derived from the spot 20-2 is stored in the storage device 14.

Before the light source 8 is moved by the XY moving device 9 to a point where a spot 20-3 at the second column of the first line can be irradiated with light after the storage of the current value derived from the spot 20-2 in the storage device 14, the sensor unit 7 is connected to the discharge device 11 by the switching device 10 to discharge the spot 20-2-derived charged current in the sensor unit 7 and the sensor unit 7 is then again connected to the ammeter 4 by the switching device 10. Thereafter, the spot 20-3 at the second column of the first line is irradiated with light, and a current value derived from the spot 20-3 is stored in the storage device 14. These steps are repeated until the detection of current derived from the final spot 20-4, and all the current values derived from all the detection spots are stored in the storage device 14.

The discharge of the charged current is preferably regulated by time. Specifically, preferably, a program of reconnection to an ammeter after connection to a discharge circuit for a given period of time is regulated by a computer 5. The above regulation of the discharge can also be applied to the discharge of charged current generated upon the contact of the working electrode and the counter electrode with the electrolyte-containing substance and to the discharge of photocurrent derived from a detection spot subjected to the latest measurement of photocurrent.

The basic principle of the detection of current derived from a sensitizing dye in a detection spot on the working electrode will be described. At the outset, a sample solution containing an analyte, a working electrode, and a counter electrode are provided. The working electrode used in the present invention is an electrode having on its surface a probe substance bindable specifically directly or indirectly to the analyte. Specifically, the probe substance may be a substance that can be specifically bound directly to an analyte, as well as a substance that can be bound specifically to a bound product obtained by binding an analyte specifically to a mediating substance such as a receptor protein molecule. Subsequently, the sample solution is brought into contact with the working electrode in the copresence of a sensitizing dye to bind the analyte specifically directly or indirectly to the probe substance and thus to immobilize the sensitizing dye on the working electrode by the binding. The sensitizing dye is a substance that can emit electrons on the working electrode in response to photoexcitation. The sensitizing dye may be previously labeled on the analyte or the mediating substance. When a sensitizing dye that can be intercalated in the analyte and the bounded product of the probe substance is utilized, the sensitizing dye may be simply added to the sample solution.

After the contact of the working electrode and the counter electrode with the electrolyte medium, the irradiation of the working electrode with light to photoexcite the sensitizing dye by the above method allows electrons to be transferred from the photoexcited sensitizing dye to an electron receiving substance. The analyte can be detected with high sensitivity by detecting photocurrent that flows across the working electrode and the counter electrode attributable to the electron transfer. Further, the detected current is highly correlated with the concentration of the analyte sample in the sample solution, and, thus, the analyte sample can be quantitatively determined based on the measured quantity of current or quantity of electricity.

Figure 6:
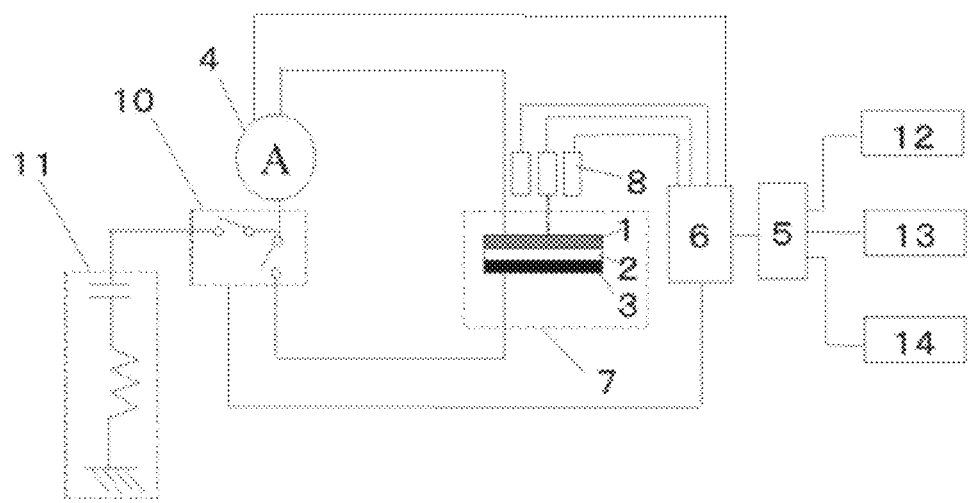
FIG. 6 is a conceptual diagram showing a basic construction of a measuring apparatus that uses an electrolyte-containing sheet and comprises a plurality of light sources or photoirradiation parts.

The measuring apparatus shown in FIG. 6 has the same construction as the measuring apparatus shown in FIG. 5, except that a plurality of light sources or light irradiation parts are provided and the XY moving device for the light source is not provided. The measuring apparatus shown in FIG. 6 comprises a plurality of light sources corresponding to respective detection spots or a plurality of light irradiation parts connected to a light source through optical fibers or the like. The timing of light irradiation from the light sources or the light irradiation parts corresponding to respective detection spots is regulated by a computer 5, and current values derived from respective detection spots are acquired by measuring current obtained upon the irradiation of the respective detection spots with light.

Figure 13:
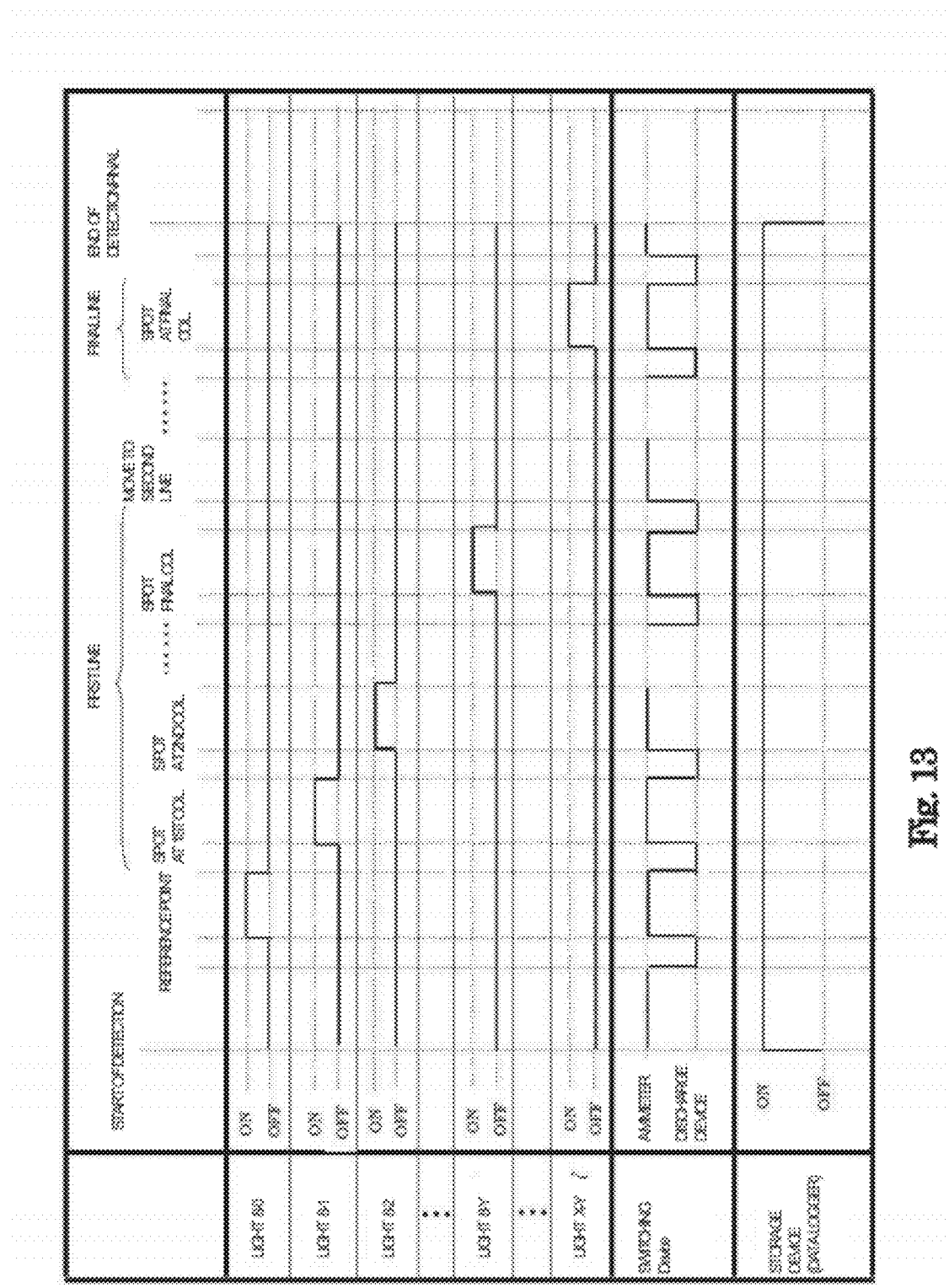
FIG. 13 is a timing chart in the detection of current in a working electrode with detection spots provided in the layout shown in FIG. 11 shown in FIG. 6.

FIG. 13 shows a timing chart when current is detected from the working electrode with detection spots provided thereon in the layout shown in FIG. 11 by the measuring apparatus shown in FIG. 6. The sensor unit 7 is first connected to the ammeter 4, and the storage device 14 for storing current values that flows across the working electrode 1 and the counter electrode 3 until the completion of the detection is started. Thereafter, the sensor unit 7 is connected to the discharge device 11 by the switching device 10. After the discharge of charged current generated in the formation of the sensor unit 7, the sensor unit 7 is again connected to the ammeter 4. A light source 8-0 is turned on for lighting to allow current derived from the reference point 20-1 to be generated, and the reference point-derived current value is stored in the storage device 14. The light source 8-0 is then turned off, and the sensor unit 7 is connected to the discharge device 11 by the switching device 10 to discharge the reference point derived charged current in the sensor unit 7. The sensor unit 7 is then again connected to the ammeter 4 by the switching device 10. A light source 8-1 is then turned on for lighting to irradiate a spot 20-2 at the first column in the first line with light, and a current value derived from the spot 20-2 is stored in the storage device 14.

After the storage of the current value derived from the spot 20-2 in the storage device 14, the light source 8-1 is turned off, and the sensor unit 7 is connected to the discharge device 11 by the switching device 10 to discharge the charged current derived from the spot 20-2 in the sensor unit 7. The sensor unit 7 is then again connected to the ammeter 4 by the switching device 10. Thereafter, the light source 8-2 is turned on for lighting to irradiate a spot 20-3 at the second column in the first line with light, and a current value derived from the spot 20-3 is stored in the storage device 14. These steps are repeated until the detection of current derived from the final spot 20-4. The current values derived from all the detection spots are stored in the storage device 14, and the analyte sample is quantitatively determined based on the measured quantity of current or quantity of electricity.

Figure 7:
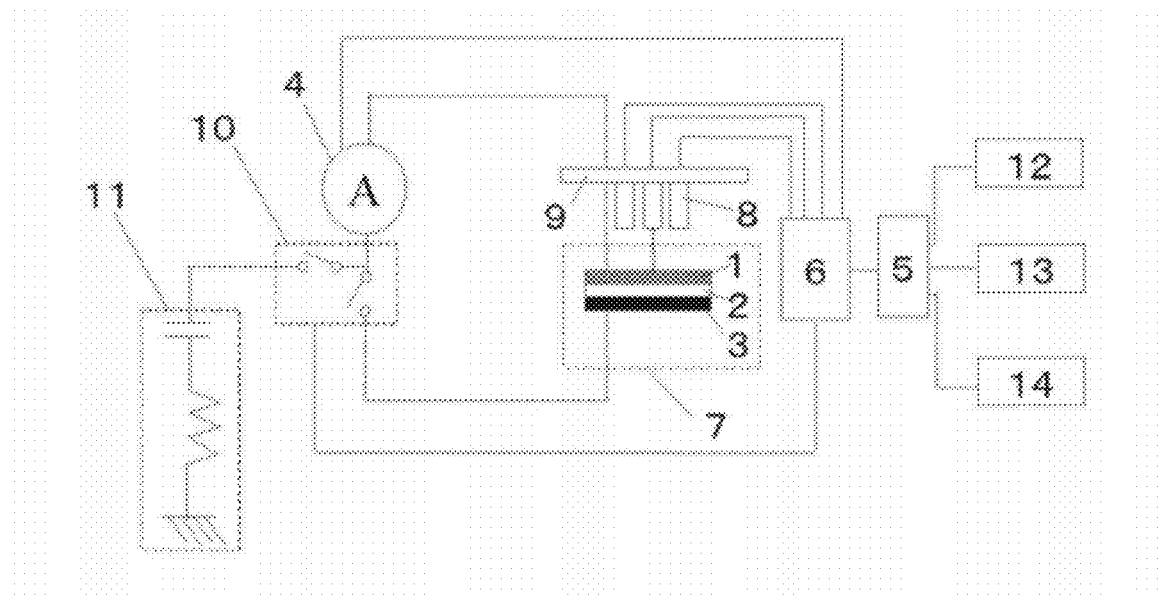
FIG. 7 is a conceptual diagram showing a basic construction of a measuring apparatus that uses an electrolyte-containing sheet and comprises a plurality of light sources or photoirradiation parts installed in an XY moving device.

The measuring apparatus shown in FIG. 7 has the same construction as the measuring apparatus shown in FIG. 5, except that the measuring apparatus shown in FIG. 7 has both a plurality of light sources or light irradiation parts 8 and an XY moving device 9. In FIG. 7, the provision of both a plurality of light sources or a plurality of light irradiation parts connected to a light source through optical fibers or the like and an XY moving device 9 can allow all of detection spots to be successively irradiated with light. The timing of light irradiation from the light sources or light irradiation parts corresponding to respective detection spots and the timing of movement of the XY moving device 9 are regulated by the computer 5, and current values of respective detection spots are acquired by measuring current obtained upon the irradiation of detection spots with light.

Figure 14:
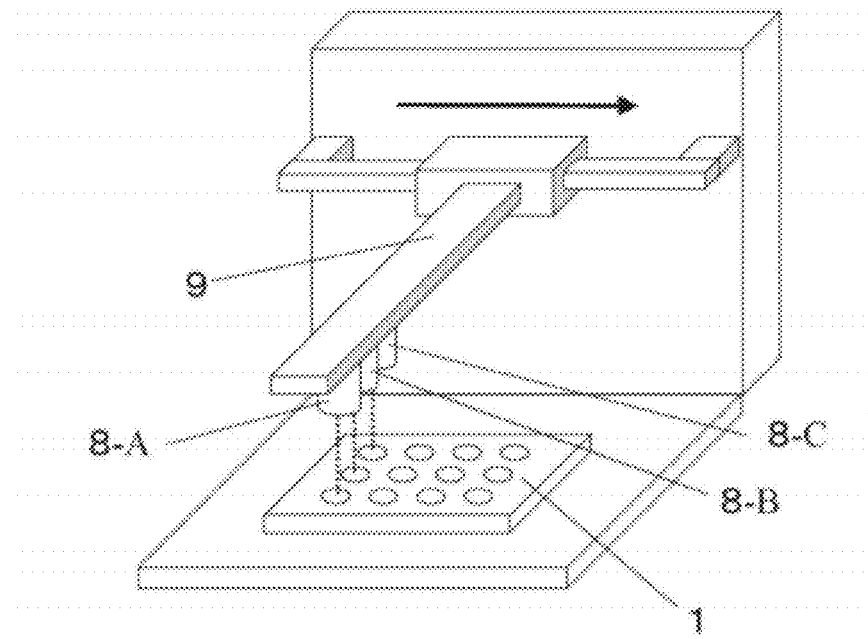
FIG. 14 is one example of the construction of the light source and the XY moving device and a layout of detection spots provided on the working electrode in the measuring apparatus shown in FIG. 7.

FIG. 14 shows the construction of the light source 8 and the XY moving device 9 in the measuring apparatus shown in FIG. 7 and an example of a layout of detection spots provided on the working electrode 1. Detection spots of 3 lines×four columns are arranged in the working electrode shown in FIG. 14. The apparatus is constructed as follows. A light source 8-A, a light source 8-B, and a light source 8-C are successively turned on for lighting. The XY moving device 9 is then moved to detection spots located on the second column. The light source 8-A, the light source 8-B, and the light source 8-C are again turned on for lighting. Thus, the light sources are turned on and turned off until detection spots located on the final column are irradiated with light. In this embodiment, however, the XY moving device 9 is monoaxial, that is, is moved only in a line direction. In the present invention, the XY moving device means a mechanism that an object such as a light source is moved horizontally in a line direction and/or a column direction of a plurality of aligned detection spots.

As shown in FIG. 14, the apparatus having a construction comprising light sources, of which the number is the same as that of columns or lines of the detection spots, and a monoaxial moving device is advantageous over a biaxial XY moving device in that the size of the apparatus can be reduced.

Figure 28:
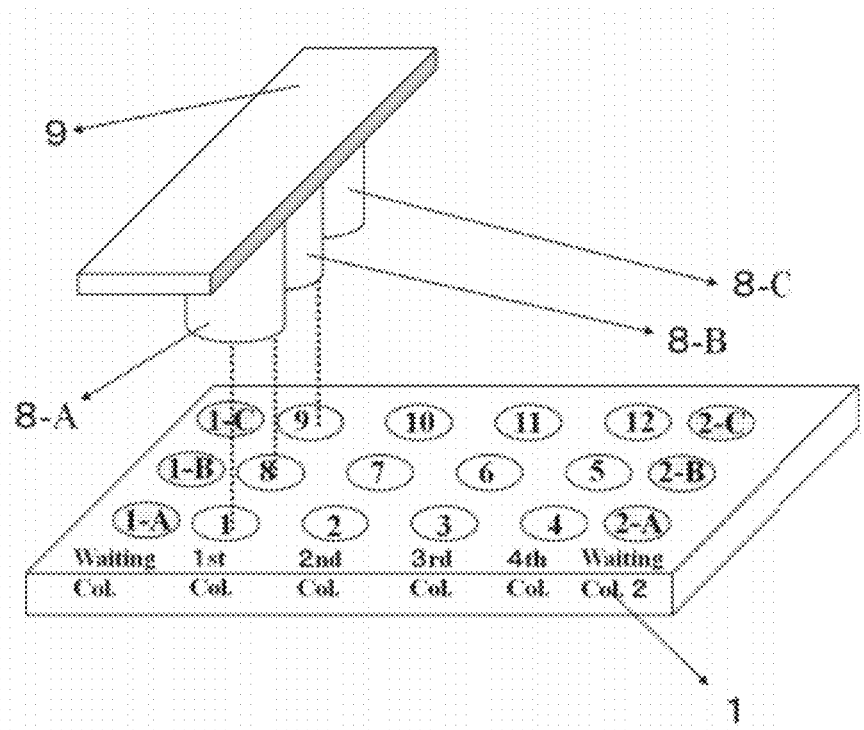
FIG. 28 is a diagram showing the detail of a light source and a layout of detection spots provided on a working electrode in the measuring apparatus shown in FIG. 14.

In another embodiment of a light irradiation method in the measuring apparatus shown in FIG. 14, the following method may also be adopted. After lighting of the light source 8-A, the light source 8-A is moved to a detection spot at the first column, a detection spot at the second column, a detection spot at the third column, and a detection spot at the fourth column in that order by a monoaxial moving device. In this case, upon the movement to each column, light irradiation and the detection of photocurrent are carried out. Thereafter, the light source 8-A is turned off, and the light source 8-B is turned on. A detection spot at the fourth column is then irradiated with light, and a detection spot at the third column, a detection spot at the second column, and a detection spot at the first column are subjected to light irradiation and the detection of photocurrent. Thereafter, the light source 8-B is turned off, and the light source 8-C is turned on for lighting. A detection spot at the first column is then irradiated with light, and a detection spot at the second column, a detection spot at the third column, and a detection spot at the fourth column are subjected to light irradiation and the detection of photocurrent. For this light irradiation method, see FIG. 28. This light irradiation method is particularly effective when laser beams or the like which require a long time for stabilization of light intensity are used. An example of a flow chart of a method for light irradiation of each detection spot is shown in Table 1 below. When the light irradiation method and the current detection method as shown in Table 1 are used, each detection spot can be irradiated in a short time with laser beams having stable light intensity. Consequently, current can be detected with high accuracy.

TABLE 1

| | |
|---|---|
| 1 | Movement of X-axis stage to waiting column 1 |
| 2 | Turning-on of light source A for lighting and waiting until light intensity of light source A becomes stable |
| 3 | Start of measurement of current |
| 4 | Movement of X-axis stage to first column and irradiation of detection spot 1 with light from light source A |
| 5 | Movement of X-axis stage to second column and irradiation of detection spot 2 with light from light source A |
| 6 | Movement of X-axis stage to third column and irradiation of detection spot 3 with light from light source A |
| 7 | Movement of X-axis stage to fourth column and irradiation of detection spot 4 with light from light source A |
| 8 | Movement of X-axis stage to waiting column 2, turning-off of light source A, turning-on of light source B for lighting, and waiting until light intensity of light source B becomes stable |
| 9 | Movement of X-axis stage to fourth column and irradiation of detection spot 5 with light from light source B |
| 10 | Movement of X-axis stage to third column and irradiation of detection spot 6 with light from light source B |
| 11 | Movement of X-axis stage to second column and irradiation of detection spot 7 with light from light source B |
| 12 | Movement of X-axis stage to first column and irradiation of detection spot 8 with light from light source B |
| 13 | Movement of X-axis stage to waiting column 1, turning-off of light source B, turning-on of light source C for lighting, and waiting until light intensity of light source C becomes stable |
| 14 | Movement of X-axis stage to first column and irradiation of detection spot 9 with light from light source C |
| 15 | Movement of X-axis stage to second column and irradiation of detection spot 10 with light from light source C |
| 16 | Movement of X-axis stage to third column and irradiation of detection spot 11 with light from light source C |
| 17 | Movement of X-axis stage to fourth column and irradiation of detection spot 12 with light from light source C |
| 18 | Turning-off of light source C |
| 19 | End of measurement of current |

Figure 8:
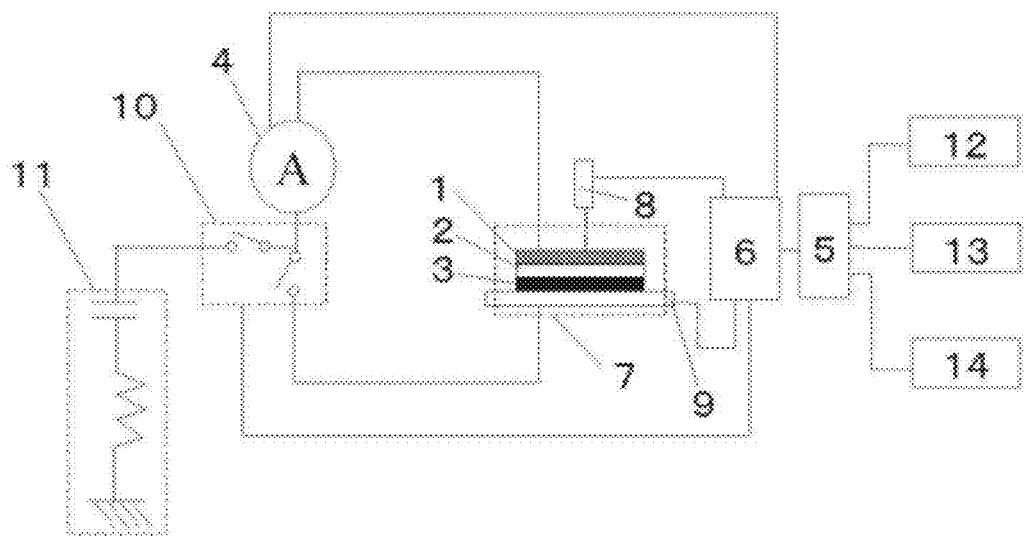
FIG. 8 is a conceptual diagram showing a basic construction of a measuring apparatus that uses an electrolyte-containing sheet and comprises a sensor cell installed in an XY moving device.
Figure 9:
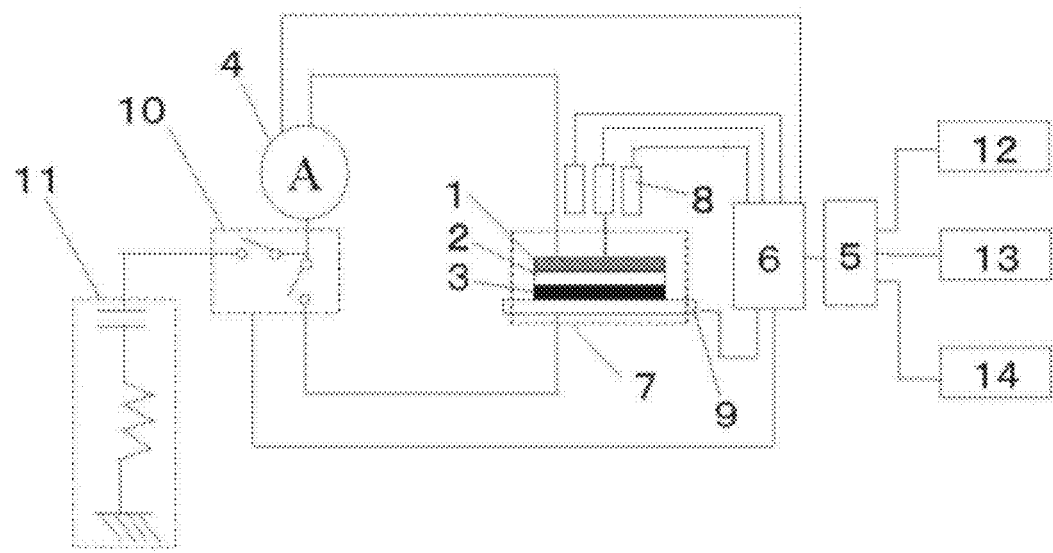
FIG. 9 is a conceptual diagram showing a basic construction of a measuring apparatus that uses an electrolyte-containing sheet and comprises a plurality of light sources or photoirradiation parts and a sensor cell installed in an XY moving device.

The measuring apparatus shown in FIG. 8 has the same construction as the measuring apparatus shown in FIG. 5, except that the sensor cell 7 is moved relative to the light source 8 by the XY moving device 9. Likewise, the measuring apparatus shown in FIG. 9 has the same construction as the measuring apparatus shown in FIG. 5, except that the apparatus comprises a combination of a plurality of light sources or light irradiation parts 8 and an XY moving device 9 and the sensor cell 7 is moved by the XY moving device 9. The timing of light irradiation from the light sources or light irradiation parts corresponding to respective spots and the timing of movement of the XY moving device 9 are regulated by the computer 5, and current values of respective detection spots are acquired by measuring current obtained upon the irradiation of detection spots with light.

The measuring apparatus shown in FIG. 10 is a measuring apparatus using an electrolysis solution as an electrolyte-containing substance. The sensor unit included in the measuring apparatus comprises a working electrode, a counter electrode, and a flow passage provided so that solutions fed come into contact with the working electrode and the counter electrode. Solutions fed are, for example, an electrolysis solution 2', a reaction solution containing a reactant that reacts specifically with a probe substance on the working electrode, and a washing solution. The solutions are fed into between the working electrode 1 and the counter electrode 3 and are discharged. The measuring apparatus further comprises a pump 16 that is used in feeding the solutions, and a valve 17 that is necessary for the regulation of the solutions fed. The pump 16 and the valve 17 are regulated by the computer 5. The apparatus may have the same construction as the measuring apparatus shown in FIG. 5, except that the measuring apparatus comprises the pump 16 and the valve 17 that are regulated by the computer 5, and a flow passage for feeding the solution into the sensor unit 7 is provided within the sensor unit 7. Any method shown in FIGS. 5 to 10 may be used for irradiation of detection spots on the working electrode 1 with light and current detection. In the measuring apparatus shown in FIG. 10, the provision of the valve 17 is not indispensable. In an embodiment where any valve is not provided, a method is preferably adopted in which switching of the solutions is carried out manually, and the solutions are fed by regulating the pump 16 with the computer 5.

Figure 15:
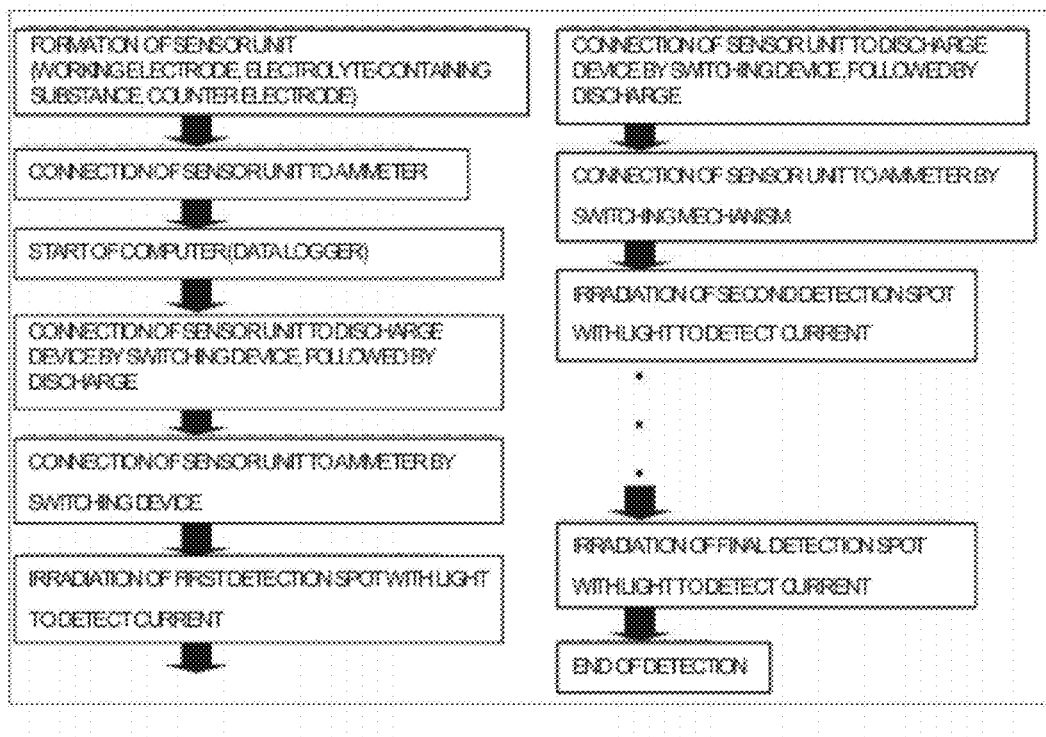
FIG. 15 is a flow chart of a photoirradiation method on detection spots provided on a working electrode and a current detection method.

The method for irradiating detection spots provided on the working electrode with light and the current detection method as described above are shown in a flow chart of FIG. 15. According to the measuring apparatus and the specific detection method of the present invention, the timing of light irradiation and the timing of connection to the ammeter and the discharge device are regulated in various light irradiation methods and sensor unit constructions to realize accurate detection.

Sensor Unit where Electrolyte-Containing Sheet is Used

Figure 16:
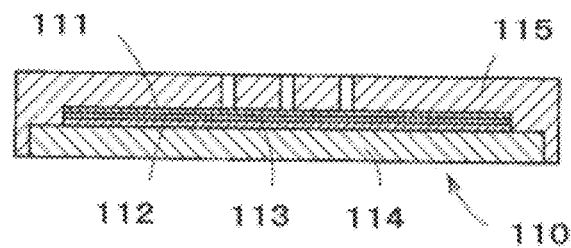
FIG. 16 is a cross-sectional view and an exploded view of a sensor unit in a first embodiment in use of an electrolyte-containing sheet according to the present invention.
Figure 16:
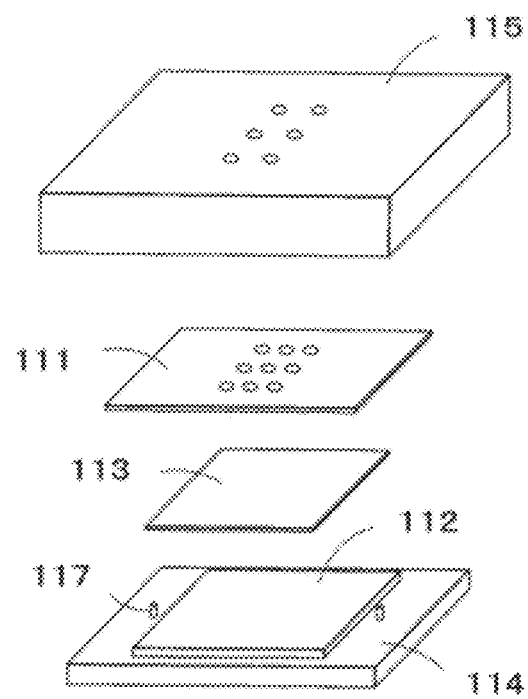

The sensor unit in a first embodiment of the present invention where an electrolyte-containing sheet is used comprises a working electrode, a counter electrode provided opposite to the working electrode, and an electrolyte-containing sheet held between the working electrode and the counter electrode, the surface of the working electrode and the surface of the counter electrode being in contact with the electrolyte-containing sheet. Specifically, the surface side of the working electrode (the side where the analyte is immobilized) and an electrically conductive surface of the counter electrode (such as platinum) face each other and are in contact with the electrolyte-containing sheet. FIG. 16 shows a cross-sectional view and an exploded view of the sensor unit in the first embodiment. In a sensor unit 110 shown in FIG. 16, a working electrode 111 is located above a counter electrode 112, and an electrolyte-containing sheet 113 is held between the working electrode 111 and the counter electrode 112. Further, the sensor unit 110 comprises a support base material 114 that supports the counter electrode 112. A pressing member 115 is provided on the uppermost part of the sensor unit 110 so that the working electrode 111, the electrolyte-containing sheet 113, and the counter electrode 112 are pressed downward toward the support base material 114 to bring them into close contact with each other. In this sensor unit, the order of stacking of components is not limited to that shown in the drawing, and the components may be stacked in the order opposite to the order shown in FIG. 16. In this case, a construction may be adopted in which a working electrode is supported on a support base material, an electrolyte-containing sheet and a counter electrode are provided in that order on the working electrode, and a pressing member is further provided so as to press the counter electrode, the electrolyte-containing sheet, and the working electrode toward the support base material and thus to bring them into close contact with each other. In the embodiment shown in the drawing, the components are horizontally disposed. Alternatively, the components may be vertically disposed. Preferably, the pressing member 115 further comprises an opening part or a light transparent part through which light is passed for photoexcitation.

Figure 17:
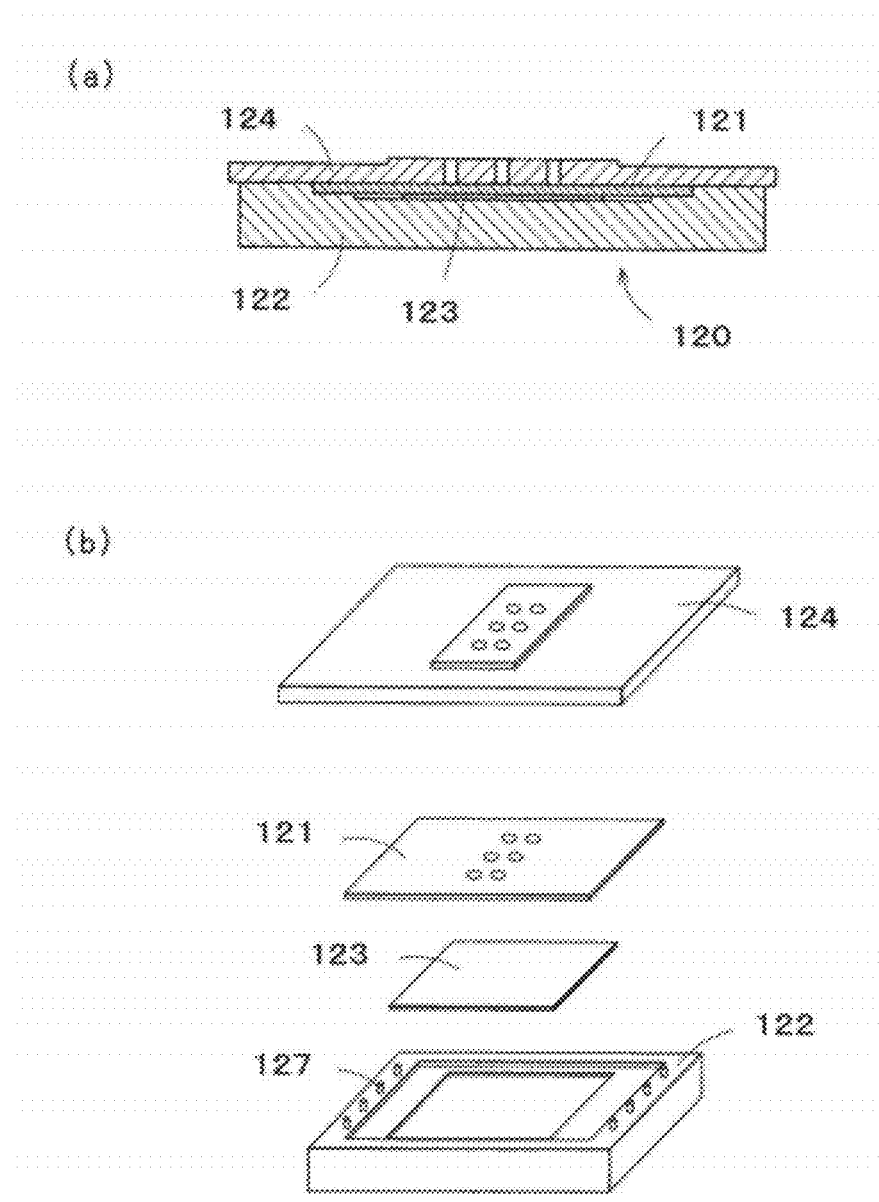
FIG. 17 is a cross-sectional view and an exploded view of a sensor unit in a second embodiment in use of an electrolyte-containing sheet according to the present invention.
Figure 18:
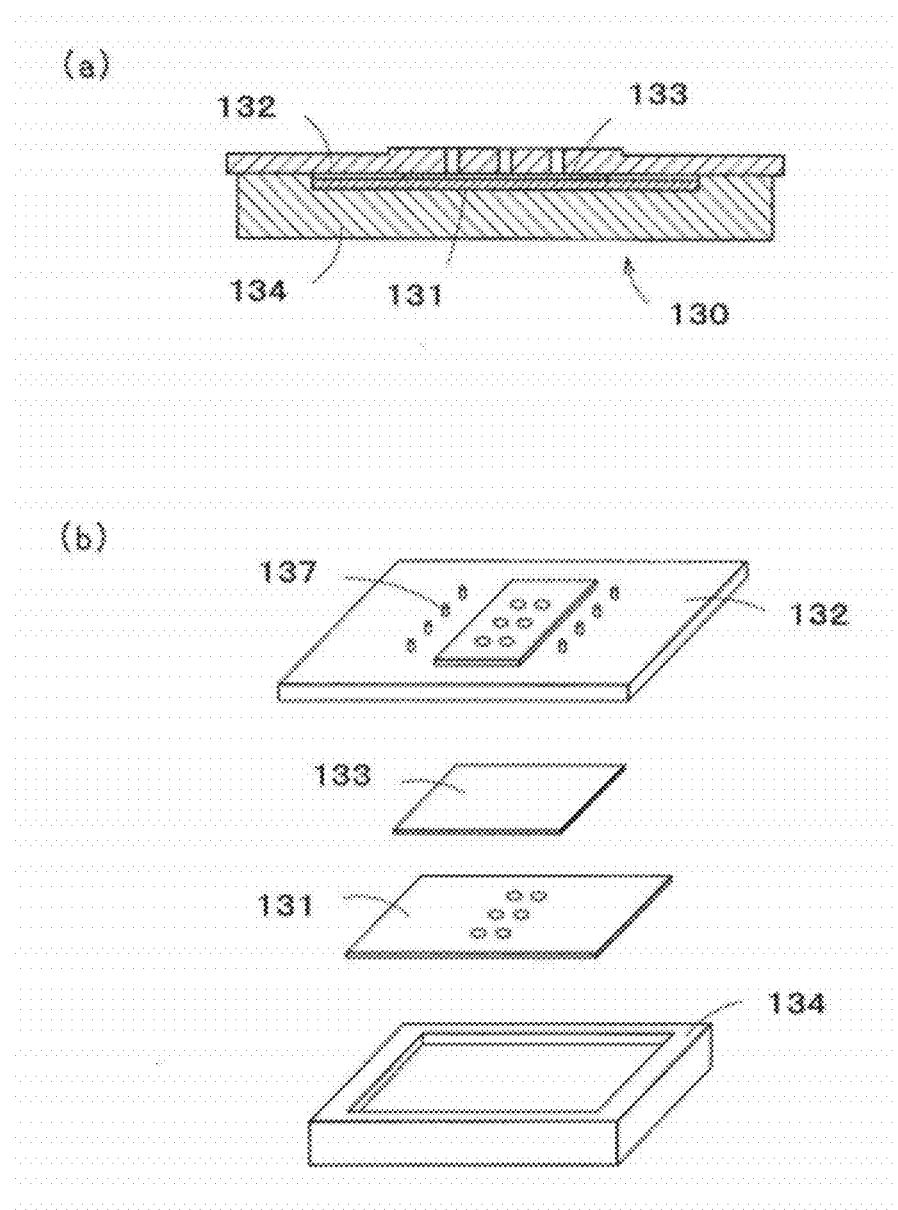
FIG. 18 is a cross-sectional view and an exploded view of a sensor unit in a second embodiment in use of an electrolyte-containing sheet according to the present invention.
Figure 19:
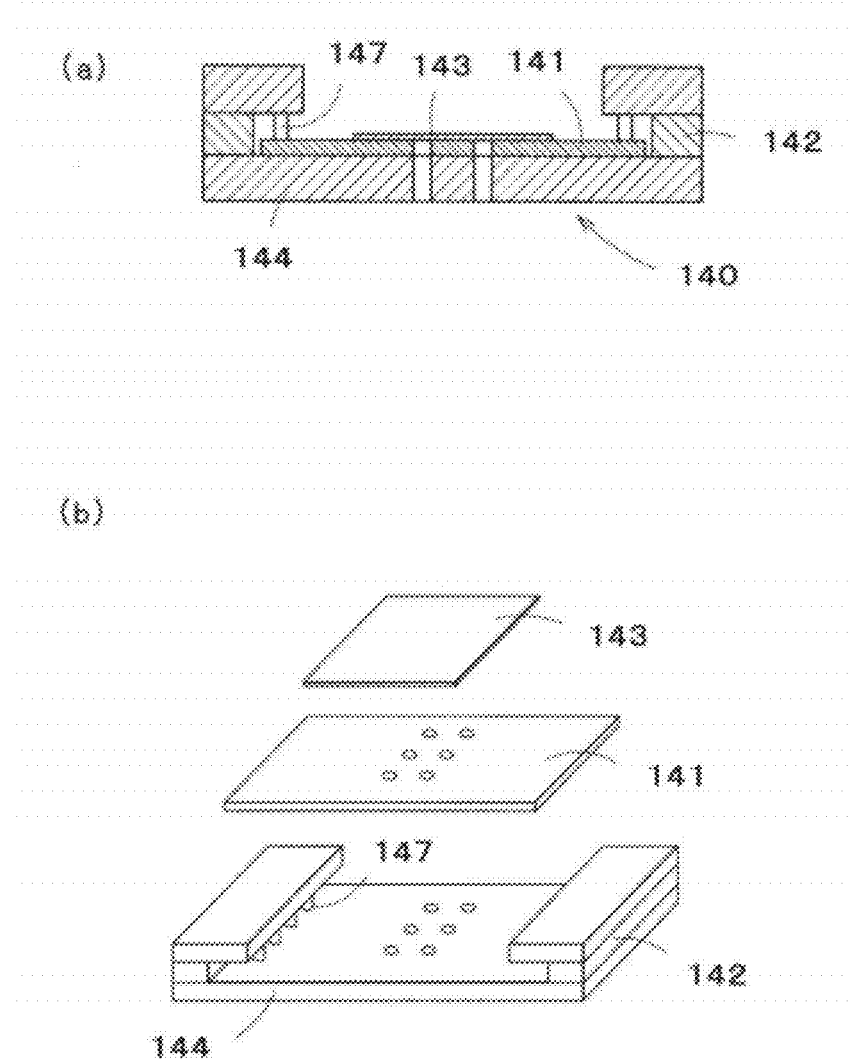
FIG. 19 is a cross-sectional view and an exploded view of a sensor unit in a second embodiment in use of an electrolyte-containing sheet according to the present invention.

The sensor unit in a second embodiment of the present invention where the electrolyte-containing sheet is used comprises: an electrode unit comprising a working electrode and a counter electrode that are patterned on an identical plane; and an electrolyte-containing sheet provided in contact with the surface of the working electrode and the surface of the counter electrode. FIGS. 17 to 19 show a cross-sectional view and an exploded view of the sensor unit in the second embodiment. In a sensor unit 120 shown in FIG. 17, a counter member 122 is provided opposite to an electrode unit 121. An electrolyte-containing sheet 123 is held between the electrode unit 121 and the counter member 122. That is, the electrode unit 121 is disposed on the electrolyte-containing sheet 123 provided on the counter member 122 so that an analyte-immobilized side of the electrode unit 121 faces downward. Further, a pressing member 24 is provided in the sensor unit 120 so as to press the electrode unit 121 and the electrolyte-containing sheet 123 toward the counter member 122 and thus to bring them into close contact with each other. On the other hand, in the sensor unit 130 shown in FIG. 18, a support base material 134 that supports the electrode unit 131 is further provided on the electrode unit 131, and a counter member 132 functions as a pressing member that presses an electrolyte-containing sheet 133 and an electrode unit 131 toward the support base material 134 to bring them into close contact with each other. That is, the electrode unit 131 is disposed on the support base material 134 so that an analyte-immobilized side of the electrode unit 131 faces upward, and the electrolyte-containing sheet 133 is disposed on the electrode unit 131. In these sensor units, the order of stacking of the components is not limited to that shown in the embodiment shown in the drawing, and the components may be stacked in an order opposite to the order shown in FIGS. 17 and 18. Further, in the embodiment shown in the drawing, the members are horizontally disposed. Alternatively, the members may be disposed in a vertical state. Preferably, the pressing members 124, 132 further comprise one or more openings or light-transparent parts through which light is passed for photoexcitation. In the sensor unit 130 shown in FIG. 18, irradiated light is passed through the electrolyte-containing sheet. Accordingly, when a colorable electrolyte or the like is used, preferably, the light source and the electrolyte concentration are properly regulated so that a problem of attenuation of light intensity does not occur. On the other hand, in the sensor unit 140 shown in FIG. 19, a support base material 144 that supports the electrode unit 141 is provided on the electrode unit 141, and a pressing member 142 is provided so as to press the electrode unit 141 toward the support base material 144 and thus to bring the electrode unit 141 into close contact with the support base material 144. Preferably, the pressing member 142 is constructed so as to cover only the end or a portion near the end of the electrode unit 141 and thus to ensure a satisfactory opened part on the electrode unit 141, whereby an electrolyte-containing sheet 143 can easily be mounted on the electrode unit 141. Further, preferably, the pressing member 142 in its part in contact with the electrode unit 141 is formed of a contact probe 147. Thus, the electrolyte-containing sheet 143 is mounted on the opened part, on the electrode unit 141 held by the pressing member 142, preferably not covered by the pressing member 142.

In the sensor units 110, 140 shown in FIGS. 16 and 19, light from a light source (not shown) is applied from the backside of and passed through a transparent working electrode 111 or electrode unit 141 and reaches the surface of the working electrode 111 or the electrode unit 141. On the other hand, in the sensor units 120, 130 shown in FIGS. 17 and 18, light from the light source is passed through an opening part in the pressing members 124, 132 and reaches the surface of the electrode units 121, 131. A photocurrent value generated upon the photoexcitation of a sensitizing dye by the light that has reached the working electrode can be detected with an ammeter. Any means may be used to connect the working electrode and the counter electrode to the ammeter without limitation. Examples of such means include direct connection of a lead wire or connection through a contact probe 117, 127, 137, 147 as in the embodiment shown in the drawing. In particular, for the working electrode which is attached and detached for each measurement, the use of the contact probe is advantageous in that the working electrode can easily be attached and detached.

Flow-Type Sensor Unit where Electrolysis Solution is Used

Figure 20:
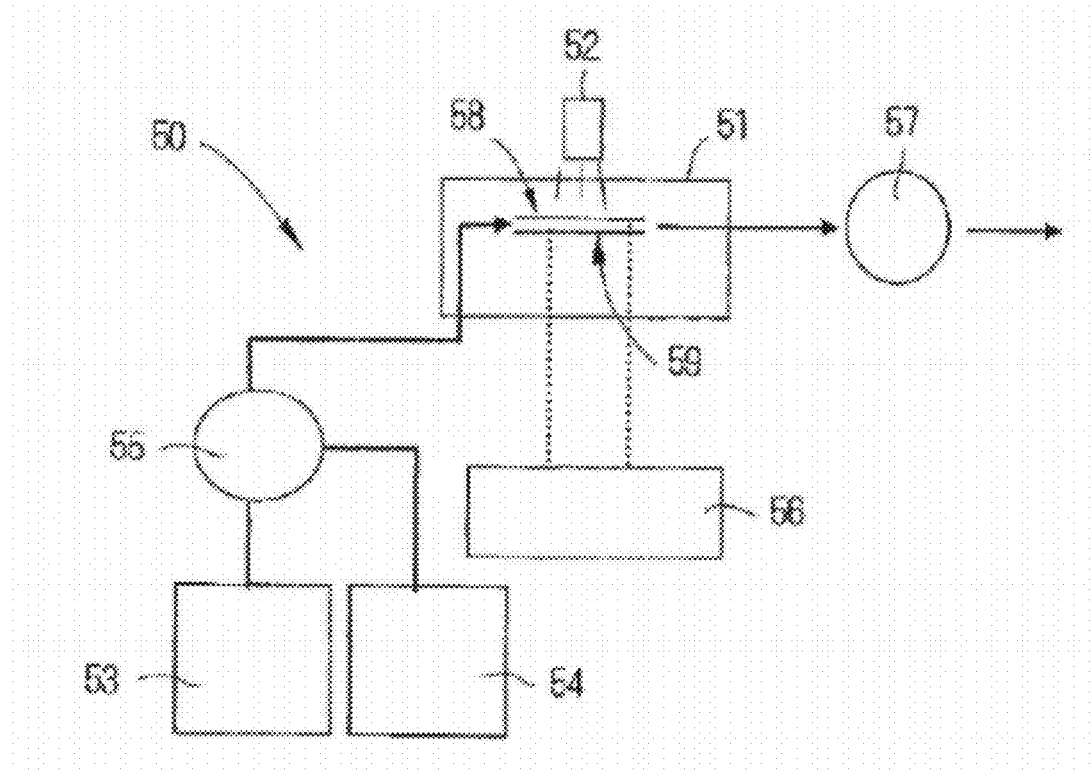
FIG. 20 is one example of a measuring apparatus using a flow-type sensor unit in use of an electrolysis solution according to the present invention.

FIG. 20 shows an example of a measuring apparatus according to the present invention using a flow-type sensor unit where an electrolysis solution is used. In a flow-type measuring sensor unit 51 shown in FIG. 20, a combination of a light source 52, an electrolysis solution tank 53, a washing solution tank 54, a feed pump 55, an ammeter 56, and a discharge pump 57 is used in the measurement. The flow-type measuring sensor unit 51 comprises a working electrode 58 and a counter electrode 59, and a flow passage is provided that can allow an electrolysis solution, a washing solution, and a reaction solution to be stored and flow so as to come into contact with a working electrode 58 and a counter electrode 59. Specifically, the flow passage is constructed so that the electrolysis solution, the washing solution, and the reaction solution fed into the measuring sensor unit 51 through the feed pump 55 are passed through the flow passage while contact with the working electrode 58 and the counter electrode 59 and are then discharged to the outside of the measuring sensor unit 51 through the discharge pump 57.

In the flow-type sensor unit according to the present invention where an electrolysis solution is used, a working electrode with an analyte, together with a sensitizing dye, being immobilized thereon, together with a counter electrode, is brought into contact with an electrolysis solution. The working electrode is irradiated with light to photoexcite the sensitizing dye, and photocurrent that flows across the working electrode and the counter electrode attributable to electron transfer from the photoexcited sensitizing dye to the working electrode is detected. The relative positional relationship between the working electrode and the counter electrode is not limited as long as the working electrode and the counter electrode are not electrically shortcircuited with each other and, at the same time, are in contact with the electrolyte medium. Specifically, the working electrode and the counter electrode may be disposed so as to face each other. Alternatively, the working electrode and the counter electrode may be disposed on an identical plane while providing a space therebetween. When the working electrode and the counter electrode are disposed on an identical plane while providing a space therebetween, preferably, both the electrodes are provided on an insulating substrate from the viewpoint of preventing electric short-circuiting between the working electrode and the counter electrode.

Figure 21:
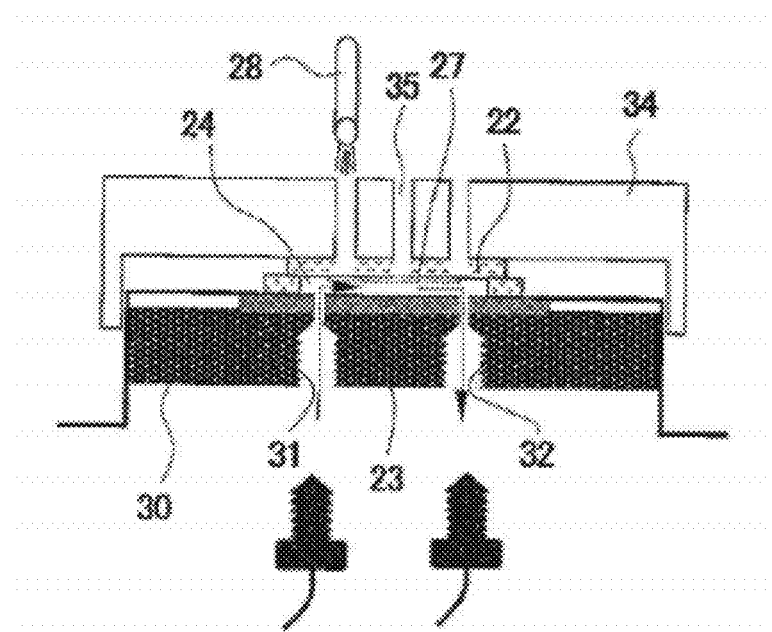
FIG. 21 is one example of a flow-type sensor unit in use of an electrolysis solution according to the present invention.

FIG. 21 shows an example of a sensor unit. In the sensor unit shown in FIG. 21, a counter electrode 23 is provided on a substrate 30. A feed hole 31 and a discharge hole 32 for an electrolysis solution or a washing solution are provided in the substrate 30. An insulating spacer 25 having a space 24 for storing the electrolysis solution is provided on the counter electrode 23. A working electrode 22 is provided on the insulating spacer 25, and a plurality of electron-receptive layers 27 are provided on the working electrode 22 in its surface that faces the space 24 while providing a space between the electron-receptive layers 27.

A contact point 33 for the working electrode is provided through the substrate 30 so that the contact point 33 does not interfere with the counter electrode 23. In the contact point 33 for the working electrode, the electrode is taken out by using, as an electric contact point, a probe bound to the electron-receptive layer 27.

A pressing member 34 is provided on the working electrode 22, and a through-hole 35 is provided at positions corresponding respectively to the plurality of electron-receptive layers 27 in the pressing member 34. Light from the light source 28 is applied to the working electrode 22 through the through-holes 35. An ammeter 36 is connected between the working electrode 22 and the counter electrode 23, and photocurrent that flows through the system upon photoirradiation is measured with the ammeter.

Electrolyte-Containing Sheet

The electrolyte-containing sheet used in the present invention is a sheet-shaped electrolyte-containing substance that is used as an electrolyte medium in specific detection of an analyte using photocurrent generated upon photoexcitation of a sensitizing dye. The electrolyte-containing sheet comprises a hydrous base material and an electrolyte contained in the hydrous base material.

In the present invention, the electrolyte is not limited as long as the electrolyte is freely moved within the hydrous base material to participate in the transfer of electrons among the sensitizing dye, the working electrode, and the counter electrode, and a wide variety of electrolytes are usable. Preferred electrolytes are substances that can function as a reducing agent (an electron donating agent) which donates electrons to the dye photoexcited by photoirradiation. Examples of such substances include sodium iodide (NaI), potassium iodide (KI), calcium iodide ($CaI_2$), lithium iodide (LiI), ammonium iodide ($NH_4I$), tetrapropyl ammonium iodide ($NPr_4I$), sodium thiosulfate ($Na_2S_2O_3$), sodium sulfite ($Na_2SO_3$), hydroquinone, $K_4[Fe(CN)_6].3H_2O$, ferrocene-1,1'-dicarboxylic acid, ferrocenecarboxylic acid, sodium borohydride ($NaBH_4$), triethylamine, ammonium thiocyanate, hydrazine ($N_2H_4$), acetaldehyde ($CH_3CHO$), N,N,N',N'-tetramethyl-p-phenylenediamine dihydrochloride (TMPD), L-ascorbic acid, sodium tellurite ($Na_2TeO_3$), iron(II) chloride tetrahydrate ($FeCl_2.4H_2O$), EDTA, cysteine, triethanolamine, tripropylamine, iodine-containing lithium iodide (I/LiI), tris(2-chloroethyl) phosphate (TCEP), dithiothreitol (DTT), 2-mercaptoethanol, 2-mercaptoethanolamine, thiourea dioxide, $(COOH)_2$, HCHO, and combination thereof. More preferred are NaI, KI, $CaI_2$, LiI, $NH_4I$, tetrapropyl ammonium iodide ($NPr_4I$), sodium thiosulfate ($Na_2S_2O_3$), and sodium sulfite ($Na_2SO_3$), and mixtures thereof. More preferred is tetrapropyl ammonium iodide ($NPr_4I$).

(1) Gel Sheet

In a preferred embodiment of the present invention, the hydrous base material is a gel matrix comprising at least one material selected from natural gel and synthetic gel, and, preferably, the electrolyte is dispersed in the gel matrix. Specifically, in this embodiment, the electrolyte-containing sheet is formed as a gel sheet.

In a preferred embodiment of the present invention, the gel sheet has a gel strength of not less than 100 g/cm$^2$, more preferably not less than 120 g/cm$^2$, still more preferably not less than 150 g/cm$^2$. When the gel strength is in the above-defined range, the gel sheet can easily be handled solely. Therefore, the gel sheet can easily be held between or can easily be removed from the working electrode and the counter electrode. Consequently, the sensor unit structure and the detection procedure can be significantly simplified.

In the present invention, regarding the form of the gel sheet, from the viewpoint of ensuring good adhesion between the gel sheet and the working electrode and between the gel sheet and the counter electrode, the part of contact with each of the electrodes is preferably smooth and planar. Accordingly, in use, when the gel sheet is held between the working electrode and the counter electrode, preferably, the gel sheet has a uniform thickness from the viewpoint of avoiding an influence of the thickness on the adhesion. On the other hand, when an electrode unit comprising a working electrode and a counter electrode that have been patterned on an identical plane is used, the adoption of a smooth and planar surface in at least one side in contact with the electrode unit suffices for contemplated results. There is no particular problem of thickness and evenness of the thickness.

In a preferred embodiment of the present invention, preferably, the gel sheet has a thickness of 0.1 to 10 mm, more preferably 0.5 to 3 mm, still more preferably 1 to 3 mm. When the thickness is in the above-defined range, a strength high enough to handle the gel sheet alone can easily be obtained. Accordingly, the gel sheet can easily be held between or removed from between the working electrode and the counter electrode or can be carried out. Consequently, the structure of the sensor unit and the detection procedure can be significantly simplified. Further, there is no adverse effect on the measurement of photocurrent.

In the present invention, the gel matrix is not limited as long as the gel matrix comprises at least one gel selected from natural gels and synthetic gels and has a suitable level of strength and adhesion to the electrode. As with conventional gels, these gels can be formed by the gelation of a gelation agent together with a solvent such as water. The concentration of the gelation agent in the gel matrix does not have a significant influence on the measurement of photocurrent. Accordingly, the concentration of the gelation agent may be properly determined depending upon the kind of the gelation agent from the viewpoint of ensuring strength high enough to allow the gel sheet to be handled alone.

In a preferred embodiment of the present invention, the gel matrix comprises a natural gel composed mainly of a polysaccharide and a protein. Preferred examples of such natural gels include agarose, alginic acid, carageenan, roast bean gum, gellan gum, gelatin, and mixtures thereof. The natural gel is more preferably agarose gel. The preferred amount of the agarose gel added is 0.5 to 25% by weight.

In another preferred embodiment of the present invention, the gel matrix comprises synthetic gel. Examples of preferred synthetic gels include polyacrylamides, polyvinyl pyrrolidones, sodium polyacrylates, PVA-added polyacrylamides, polyethylene oxides, N-alkyl-modified (meth)acrylamide derivatives, N,N-dimethylacrylamides, N,N-diethylacrylamides, acryloylmorpholines, N-methylacrylamides, N-ethylacrylamides, N-(iso)propylacrylamides, N-butylacrylamides, N-hydroxymethylacrylamides, N-hydroxyethylacrylamides, N-hydroxypropylacrylamides, N-hydroxybutylacrylamides, (meth)acrylic acid, t-butyl (meth)acrylamide sulfonic acid, sulfopropyl(meth)acrylate, (meth)acrylic acid, itaconic acid, (poly)alkylene glycol (meth)acrylate, hydroxyethyl(meth)acrylate, polyethylene glycol(meth)acrylate, hydroxypropyl(meth)acrylate, polypropylene glycol(meth)acrylate, glycerin(meth)acrylate, methylenebis(meth)acrylamides, ethylenebis(meth)acrylamides, (poly)ethylene glycol di(meth)acrylate, (poly)propylene glycol dimeth)acrylate, glycerin di(meth)acrylate, glycerin tri(meth)acrylate, tetraallyloxyethane, and mixtures thereof. More preferred are polyacrylamide gels.

In a preferred embodiment of the present invention, the gel sheet according to the present invention may be produced by (1) a process comprising adding an electrolyte and a gelation agent to water, heat-dissolving the mixture to prepare gel and then processing the gel into a desired sheet shape or (2) a process comprising forming gel using a gelation agent alone, processing the gel into a desired sheet shape, and then immersing the gel sheet in an electrolysis solution to disperse the electrolyte in the gel. In particular, a combination of the gelation agent with some electrolyte sometimes does not gel by mixing, heating or cooling. Even in this case, the gel sheet can be prepared by the method (2).

(2) Water-Absorptive Sheet

In another preferred embodiment of the present invention, the hydrous base material is a water-absorptive base material. Specifically, in this embodiment, the electrolyte-containing sheet is formed as a water-absorptive sheet. When the water-absorptive sheet is used as the electrolyte medium, a detection sensitivity and a detection accuracy similar to those obtained when the electrolysis solution is used are obtained. That is, when the water-absorptive sheet is used, photocurrent can be detected with high accuracy.

In a preferred embodiment of the present invention, the water-absorptive sheet has a water content of not less than 20%, more preferably not less than 30%, still more preferably not less than 40%. When the water content is in the above-defined range, high photocurrent can be detected in the detection of photocurrent, contributing to improved detection sensitivity. The water content is determined by (amount of water per mm$^3$)/(density of water-absorptive base material). The water content referred to herein is a water content of the water-absorptive sheet in the detection of photocurrent and, as will be described below, may not satisfy the above-defined water content requirement during storage.

In the water-absorptive sheet according to the present invention, the part of the contact between the water-absorptive sheet and each of the working electrode and the counter electrode is smooth and planar from the viewpoint of ensuring close contact with the working electrode and the counter electrode. Accordingly, when the water-absorptive sheet is held, in use, between the working electrode and the counter electrode, preferably, the water-absorptive sheet takes a form having a uniform thickness to avoid an influence on the adhesion. On the other hand, when an electrode unit comprising a working electrode and a counter electrode that are patterned on an identical plane is used, what is required is that the water-absorptive sheet at least in its one surface in contact with the electrode unit is a smooth and planar surface. In this case, the thickness and the uniformity of the thickness do not pose any problem.

In a preferred embodiment of the present invention, the water-absorptive sheet has a thickness of 0.01 to 10 mm, more preferably 0.1 to 3 mm. When the thickness is in the above-defined range, a strength suitable for handling the water-absorptive sheet alone can easily be obtained. Accordingly, the water-absorptive sheet can easily be held between or removed from between the working electrode and the counter electrode or can be carried. Consequently, the structure of the sensor unit and the detection procedure can be significantly simplified. Further, there is no adverse effect on the measurement of photocurrent.

In the present invention, preferably, the water-absorptive base material comprises at least one kind of fiber selected from natural fibers such as cotton, hemp, wool, silk, and cellulose; pulp fibers used in filter papers, papermaking and the like; regenerated fibers such as rayon; glass fibers used in filter papers and the like; and synthetic fibers used in felts, sponges and the like, and is not limited as long as the water-absorptive base material has a suitable level of strength, water content, and adhesion to the electrode. The fibers used in the water-absorptive base material according to the present invention may be processed by any processing method without limitation.

In a preferred embodiment of the present invention, examples of preferred water-absorptive base materials include filter papers, membrane filters, glass filters, and filter cloths. More preferred are filter papers and membrane filters.

In a preferred embodiment of the present invention, the electrolyte-containing absorptive sheet according to the present invention may be treated before use by (1) a method that comprises, after processing into a desired sheet shape, immersing the sheet in a water-based electrolysis solution, or (2) a method that comprises, after processing into a desired sheet shape, immersing the sheet in an electrolysis solution, drying the sheet, and then dropping water on the dried sheet immediately before use of the sheet.

Electrolysis Solution

The electrolysis solution used in the present invention comprises an electrolyte, at least one solvent selected from aprotic solvents and protic solvents, and optionally additives. The electrolyte is the same as that used in the electrolyte-containing sheet, and the solvent is an aprotic solvent, a protic solvent, or a mixture thereof. Specifically, polar solvent types that are composed mainly of water and contain a buffer solution component mixed therewith, and aprotic polar solvents may be used. Aprotic polar solvents usable herein include nitriles such as acetonitrile, carbonates such as propylene carbonate and ethylene carbonate, heterocyclic compounds such as 1,3-dimethylimidazolinone, 3-methyloxazolinone, and dialkylimidazoliums, dimethylformamide, dimethylsulfoxide, and sulfolane. A plurality of kinds of solvents may be used as the solvent contained in the electrolyte medium, and, in actual use, the composition of the solvent may be properly varied depending upon a detection object.

Light Source

In the present invention, the light source used is not limited as long as the light source can apply light with wavelengths that can photoexcite a labeled dye. Examples of preferred light sources include fluorescent lamps, black lights, bactericidal lamps, incandescent lamps, low-pressure mercury lamps, high-pressure mercury lamps, xenon lamps, mercury-xenon lamps, halogen lamps, metal halide lamps, LEDs (white, blue, green, and red), laser beams ($CO_2$ laser, dye laser, and semiconductor laser), and sunlight. More preferred are fluorescent lamps, incandescent lamps, xenon lamps, halogen lamps, metal halide lamps, LEDs (white, blue, green, and red), sunlight and the like. If necessary, light having a specific wavelength region may be applied using a spectrometer or a bandpass filter.

In a preferred embodiment of the present invention, when a plurality of kinds of analytes are individually detected using two or more types of sensitizing dyes that can be photoexcited at respective different wavelengths, the plurality of dyes can be individually excited by applying light with a specific wavelength through a wavelength selecting means from the light source. Examples of wavelength selecting means include spectrometers, color glass filters, interference filters, and bandpass filters. A plurality of light sources that can apply lights with different wavelengths depending upon the type of the sensitizing dyes may be used. In this case, an example of a preferred light source is a laser beam or LED that can apply light with a specific wavelength. Further, light may be guided using quartz, glass, or a liquid light guide for efficiently applying light to the working electrode.

Analyte and Probe Substance

Various substances having specific bindability may be possible for the analyte in the present invention without limitation. In the case of such analytes, when a probe substance that can be bound specifically either directly or indirectly to the analytes is supported on the surface of the working electrode, the analytes can be detected through specific binding of the analytes directly or indirectly to the probe substance.

That is, in the present invention, the analyte and the probe substance that can be specifically bound to each other can be selected. Specifically, in a preferred embodiment of the present invention, the analyte is a specifically bindable substance, and a substance that can be specifically bound to the analyte is supported as the probe substance on the working electrode. According to this preferred embodiment, the analyte can be detected through specific binding of the analyte directly onto the working electrode. Examples of preferred combination of the analyte with the probe substance in this embodiment include a combination of a single stranded nucleic acid with a single stranded nucleic acid complementary to a nucleic acid and a combination of an antigen with an antisubstance.

Figure 22:
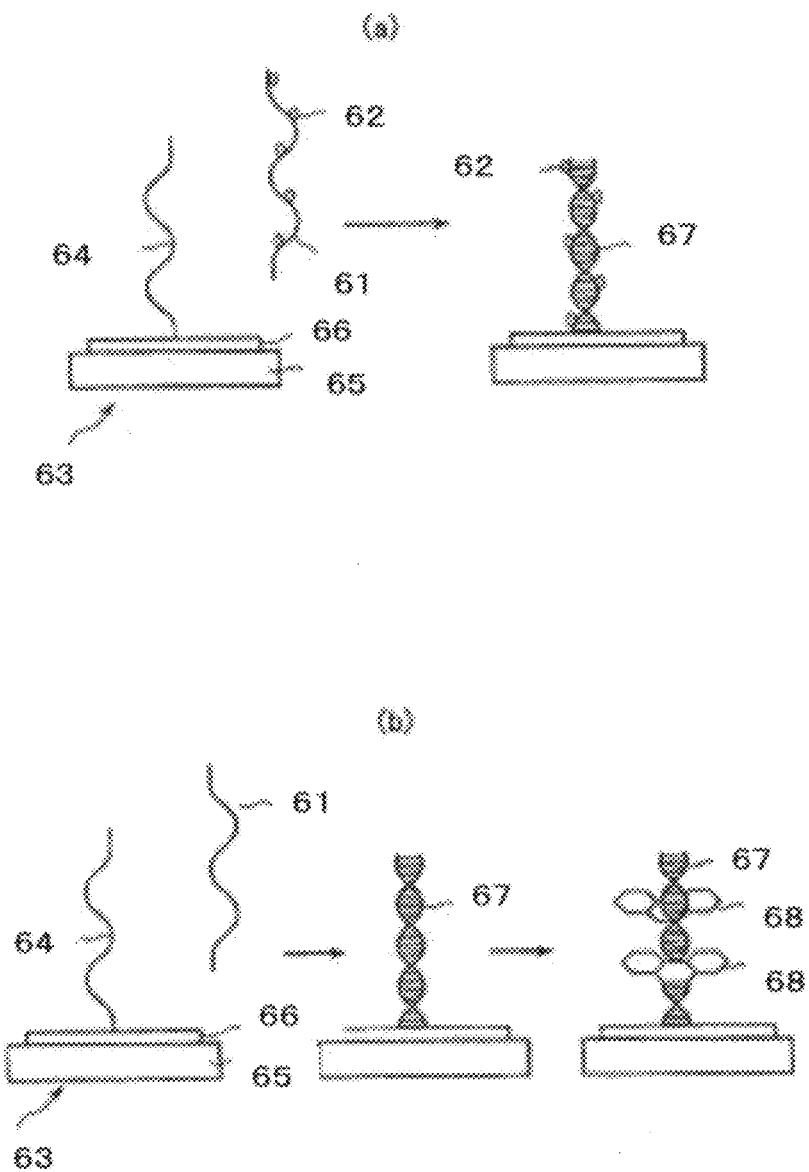
FIG. 22 is a diagram showing a step of immobilizing an analyte on a probe substance in the case where the analyte is a single stranded nucleic acid and the probe substance is a single stranded nucleic acid complementary to the nucleic acid, wherein (a) is a diagram in the case where the analyte has been previously labeled with a sensitizing dye and (b) is a diagram in the case where a sensitizing dye intercalationable into a double stranded nucleic acid has been added.

In a more preferred embodiment of the present invention, the analyte is a single stranded nucleic acid, and the probe substance is a single stranded nucleic acid complementary to a nucleic acid. The step of specifically binding the analyte to the working electrode in this embodiment is shown in FIGS. 22 (*a*) and (*b*). As shown in these drawings, a single stranded nucleic acid 1 as the analyte is hybridized with a complementary single stranded nucleic acid 64 as the probe substance supported on the working electrode 63 to form a double stranded nucleic acid 67.

When the analyte is a single stranded nucleic acid, the presence of a portion complementary to the nucleic acid as the probe substance suffices for contemplated results. The length of base pairs constituting the analyte is not limited. Preferably, however, the length of the probe substance in its parts complementary to the nucleic acid is not less than 15 bp. According to the method of the present invention, when the nucleic acid has a relatively large chain length of base pair of 200 bp, 500 bp, and 1000 bp, the formation of specific binding between the nucleic acid of the probe substance and the nucleic acid of the analyte can be detected as photocurrent with high sensitivity.

A sample solution containing a single stranded nucleic acid as an analyte can be prepared from various analyte samples containing a nucleic acid, for example, bloods such as peripheral vein bloods, leukocytes, serums, urine, faeces, semen, saliva, culture cells, and tissue cells such as various organ cells by conventional methods. At that time, the cells in the analyte sample can be destructed, for example, by externally applying physical action such as shaking or ultrasonic waves to vibrate the carrier. The nucleic acid can be liberated from the cells using a nucleic acid extraction solution. Examples of nucleic acid eluting solutions include solutions containing surfactants such as SDS, Triton-X, or Tween-20, saponin, EDTA, protease or the like. When the nucleic acid is eluted with these solutions, the reaction can be accelerated by incubation at a temperature of 37° C. or above.

In a more preferred embodiment of the present invention, when the content of the gene as the analyte is very low, a method is preferably adopted in which detection is carried out after amplification of the gene by a conventional method. A representative method for amplifying the gene would be a method using an enzyme such as a polymerase chain reaction (PCR). Examples of enzymes used in the gene amplification include DNA-dependent DNA polymerases such as DNA polymerases and Taq polymerases, DNA-dependent RNA polymerases such as RNA polymerases and RNA-dependent RNA polymerases such as Qβ replicases. A PCR method using a Taq polymerase is preferred because the amplification can be repeated by simply adjusting the temperature.

In a preferred embodiment of the present invention, in the amplification, the nucleic acid can be specifically labeled with a sensitizing dye. In general, the labeling can be carried out by the uptake of aminoallyl-modified dUTP in DNA. The efficiency of uptake of the molecule is the same as that of unmodified dUTP. At the subsequent coupling stage, the fluorescent dye activated by N-hydroxysuccinimide is specifically reacted with the modified dUTP to obtain an analyte labeled uniformly with the sensitizing dye.

In a preferred embodiment of the present invention, at the outset, a crude extracted liquid of the nucleic acid obtained as described above or a purified nucleic acid is heat-denatured at 90 to 98° C., preferably 95° C. or above, to prepare a single stranded nucleic acid.

Figure 23:
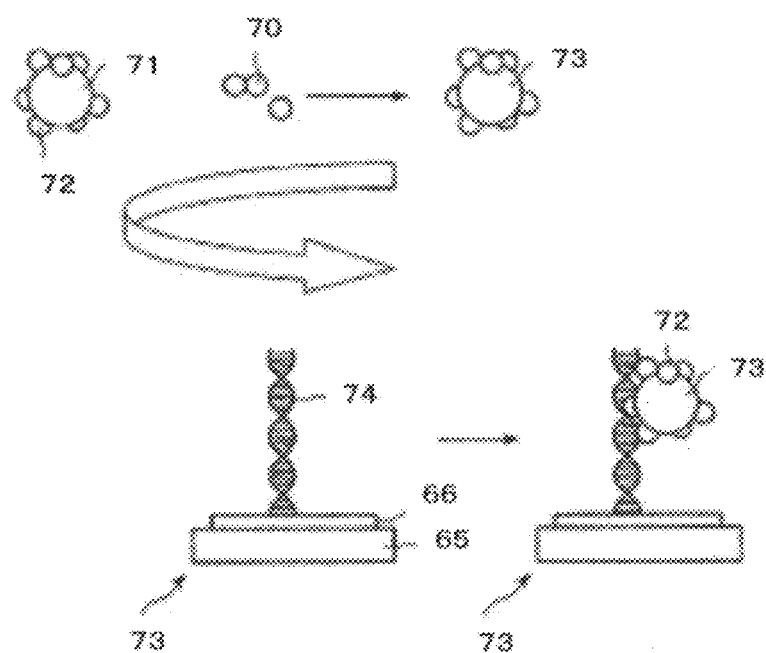
FIG. 23 is a diagram showing a step of immobilizing an analyte on a probe substance in the case where the analyte is a ligand a mediating substance is a receptor protein molecule, and a probe substance is a double stranded nucleic acid.

In the present invention, the analyte and the probe substance may be such that they are specifically bound indirectly to each other. That is, in another preferred embodiment of the present invention, the analyte is a specifically bindable substance, a substance bindable specifically to the analyte is copresent as a mediating substance, and a substance bindable specifically to the mediating substance is supported as a probe substance on the working electrode. According to this preferred embodiment, even a substance that cannot be specifically bound to the probe substance can be detected through specific binding indirectly to the working electrode through the mediating substance. Examples of preferred combinations of the analyte, the mediating substance, and the probe substance in this embodiment include a combination of a ligand, a receptor protein molecule that can receive the ligand, and a double stranded nucleic acid that can be specifically bound to the receptor protein molecule. Examples of preferred ligand include exogenous endocrine disrupting chemicals (environmental hormones). Exogenous endocrine disrupting chemicals are substances that are bound to DNA through the receptor protein molecule to affect gene expression and thus to cause toxicity. According to the method of the present invention, the bindability of a protein such as a receptor to DNA provided by the analyte can be simply monitored. The step of specific binding of the analyte to the working electrode in this embodiment is shown in FIG. 23. As shown in FIG. 23, a ligand 70 as the analyte is first specifically bound to a receptor protein molecule 71 as the mediating substance. The receptor protein molecule 73 to which the ligand 70 has been bound is specifically bound to a double stranded nucleic acid 74 as a probe substance.

According to the present invention, an analyte derived from a contemplated route through which the analyte is obtained can be quantitatively determined by simultaneously reacting one probe substance with a plurality of identical analytes derived from different route through which the analytes are obtained, and determining a difference in the amount of analyte between samples. A specific example of application of this method is an expression profile analysis by competitive hybridization on a microarray. In this analysis, analytes labeled with respective different fluorescent dyes are competitively hybridized with an identical probe substance to analyze a difference in expression pattern of a specific gene between cells. In the present invention, the use of the technique can offer an advantage unattainable by the prior art that a difference in expression between cells can be electrochemically analyzed.

Sensitizing Dye

In the present invention, in order to detect the presence of an analyte with photocurrent, the analyte is specifically bound directly or indirectly to a probe substance in the copresence of a sensitizing dye to immobilize the sensitizing dye to the working electrode through the binding. For this reason, in the present invention, as shown in FIG. 22 (a) and FIG. 23, an analyte 61 or a mediating substance 71 is previously labeled with a sensitizing dye 62. As shown in FIG. 22 (b), when a sensitizing dye 68 intercalatable in a product of binding between the analyte and the probe substance 67 (for example, a double stranded nucleic acid after hybridization) is used, the sensitizing dye can be immobilized on the probe substance by adding the sensitizing dye to the sample solution.

In a preferred embodiment of the present invention, when the analyte is a single stranded nucleic acid, one analyte molecule is labeled with one sensitizing dye. The labeling position of the single stranded nucleic acid is preferably either 5' end or 3' end of the single stranded nucleic acid from the viewpoint of easily forming specific binding between the analyte and the probe substance. The 5' end is more preferred from the viewpoint of further simplifying the labeling step.

In another preferred embodiment of the present invention, one analyte molecule is labeled with two or more sensitizing dyes from the viewpoint of enhancing the amount of the sensitizing dye supported per analyte molecule. According to this preferred embodiment, the amount of the dye supported per unit specific surface area in the working electrode with an electron receiving substance formed thereon can be increased, and, consequently, the response of photocurrent can be observed with high sensitivity.

The sensitizing dye used in the present invention may be a substance that can release electrons into the working electrode in response to photoexcitation, can be transited to a photoexcited state upon light irradiation from the light source, and can take, from the excited state, such an electron state that electrons can be injected into the working electrode. Accordingly, since the sensitizing dye used may be any sensitizing dye that can take the above electron state between the sensitizing dye and the working electrode, particularly the electron receptive layer, various sensitizing dyes are usable and there is no need to use expensive dyes.

In the embodiment wherein a plurality of analytes are individually detected, sensitizing dyes for labeling on respective analytes may be those that can be excited with lights having respectively different wavelengths, for example, may be those that can separately excite the analytes by selecting the wavelength of irradiation light. For example, even when a plurality of probes are present on an identical spot, signals can be individually detected by using a plurality of sensitizing dyes corresponding to a plurality of analytes and irradiating sensitizing dyes with respectively different excitation wavelength lights. In the present invention, the number of analytes is not limited. When the wavelength of light applied from the light source and the absorption properties of the sensitizing dye are taken into consideration, however, one to five kinds of analytes would be suitable. Sensitizing dyes usable in this embodiment may be those that can be photoexcited in a wavelength range of irradiation light, and it is not necessarily required that the absorption maximum is in the wavelength range. Whether or not there is a light absorption reaction of the sensitizing dye at a specific wavelength can be determined with a ultraviolet-visible spectrophotometer (for example, UV-3150 manufactured by Shimadzu Corporation).

Specific examples of sensitizing dyes include metal complexes and organic dyes. Examples of preferred metal complexes include metal phthalocyanines such as copper phthalocyanine and titanylphthalocyanine; chlorophyll or derivatives thereof; and hemin, complexes of ruthenium, osmium, iron and zinc described in JP H1 (1989)-220380A and JP H5 (1993)-504023T (for example, cis-dicyanate-bis (2,2'-bipyridyl-4,4'-dicarboxylate)ruthenium(II)). Examples of preferred organic dyes include metal-free phthalocyanine, 9-phenylxanthene dyes, cyanine dyes, metallocyanine dyes, xanthene dyes, triphenylmethane dyes, acridine dyes, oxazine dyes, coumarin dyes, merocyanine dyes, rhodacyanine dyes, polymethine dyes, and indigoid dyes. Examples of another preferred sensitizing dyes include Cy3, Cy3.5, Cy5, Cy5.5, Cy7, Cy7.5, and Cy9 manufactured by Amersham Biosciences; AlexaFluor355, AlexaFluor405, AlexaFluor430, AlexaFluor488, AlexaFluor532, AlexaFluor546, AlexaFluor555, AlexaFluor568, AlexaFluor594, AlexaFluor633, AlexaFluor647, AlexaFluor660, AlexaFluor680, AlexaFluor700, and AlexaFluor750 manufactured by Molecular Probes; and DY-610, DY-615, DY-630, DY-631, DY-633, DY-635, DY-636, EVOblue10, EVOblue30, DY-647, DY-650, DY-651, DYQ-660, and DYQ-661 manufactured by Dyomics.

Examples of preferred sensitizing dyes intercalatable in a double stranded nucleic acid include acridine orange and ethidium bromide. When such sensitizing dyes are used, a double stranded nucleic acid labeled with a sensitizing dye can be formed by simply adding the sensitizing dyes to a sample solution after the hybridization of the nucleic acid. Accordingly, there is no need to previously label the single stranded nucleic acid.

Working Electrode and Production Thereof

The working electrode used in the present invention is an electrode that has the probe substance on its surface and can receive electrons released by the sensitizing dye, immobilized through the probe substance, in response to photoexcitation. Accordingly, any construction and material can be adopted without limitation in the working electrode as long as the electron transfer occurs between the working electrode and the sensitizing dye used.

In a preferred embodiment of the present invention, the working electrode comprises an electron-receptive layer comprising an electron receiving substance that can receive electrons released by the sensitizing dye in response to photoexcitation, and the electron-receptive layer has a probe substance on its surface. In a more preferred embodiment of the present invention, the working electrode further comprises an electroconductive base material, and an electron-receptive layer is provided on the electroconductive base material. The electrode in this embodiment is shown in FIGS. 22 and 23. In FIGS. 22 and 23, a working electrode 63 comprises an electroconductive base material 65 and an electron-receptive layer 66 that is provided on the electroconductive base material 65 and comprises an electron receiving substance. A probe substance 64 is supported on a surface of the electron-receptive layer 66.

In the present invention, the electron-receptive layer 66 comprises an electron receiving substance that can receive electrons released by the sensitizing dye, immobilized through the probe substance 64, in response to photoexcitation. That is, the electron-receiving substance is a substance that can take an energy level on which electrons from the photoexcited labeled dye can be injected. Here the energy level (A) on which electrons from the photoexcited labeled dye can be injected means, when a semiconductor is used as the electron receiving material, a conduction band (CB). That is, the electron receiving substance used in the present invention may be any substance that the level of A is baser than the energy level of LUMO of the sensitizing dye, in other words, lower than the energy level of LUMO of the sensitizing dye.

Electron receiving substances include element semiconductors such as silicon and germanium; oxide semiconductors such as titanium, tin, zinc, iron, tungsten, zirconium, hafnium, strontium, indium, cerium, yttrium, lanthanum, vanadium, niobium, and tantalum; perovskite semiconductors such as strontium titanate, calcium titanate, sodium titanate, barium titanate, and potassium niobate; sulfide semiconductors such as cadmium sulfide, zinc sulfide, lead sulfide, silver sulfide, antimony sulfide, and bismuth sulfide; selenide semiconductors such as cadmium selenide and lead selenide; cadmium telluride semiconductors; phosphide semiconductors such as zinc phosphide, gallium phosphide, indium phosphide, and cadmium phosphide; and compound semiconductors such as gallium arsenide, copper-indium-selenide, and copper-indium-sulfide. The semiconductor listed above may be any of intrinsic semiconductors and impurity semiconductors.

On the other hand, in a preferred embodiment of the present invention, the electron receiving substance is an oxide semiconductor. More preferred are $TiO_2$, $ZnO$, $SnO_2$, $Fe_2O_3$, $WO_3$, $Nb_2O_5$, $Ta_2O_3$, $In_2O_3$, and strontium titanate. Most preferred are $TiO_2$, indium-tin composite oxides (ITO), and fluorine-doped tin oxide (FTO). ITO and FTO can function as an electron-receptive layer and also as an electroconductive base material. Accordingly, when these materials are used, the electron-receptive layer even when they are used solely, can function as the working electrode without using any electroconductive base material.

When the semiconductor is used as the electron receiving substance, the semiconductor may be either a single crystal or a polycrystal. The polycrystal is preferred, and a porous semiconductor rather than a dense semiconductor is preferred. According to this embodiment, the specific surface area is increased, and, consequently, a larger amount of the analyte and the sensitizing dye can be adsorbed, contributing to the detection of an analyte with higher sensitivity. Accordingly, in a preferred embodiment of the present invention, the electron-receptive layer is porous and has pore diameters of 3 to 1000 nm, more preferably 10 to 100 nm.

In a preferred embodiment of the present invention, the surface area in such a state that the electron-receptive layer is provided on the electroconductive base material is not less than 10 times, more preferably 100 times, larger than the projected area. The upper limit of the surface area is not particularly limited and would be generally approximately 1000 times. The diameter of fine particles of the electron receiving substance constituting the electron-receptive layer is preferably 5 to 200 nm, more preferably 8 to 100 nm, still more preferably 20 to 60 nm as primary particles in terms of average particle diameter using diameters obtained by converting the projected area to a circle. The average diameter of fine particles (secondary particles) of the electron receiving substance in a dispersion is preferably 0.01 to 100 µm. From the viewpoint of scattering incident light to improve light capture, the electron receiving substance having the above diameter may be used in combination with fine particles of an electron receiving substance having a larger particle size of, for example, about 300 nm to form the electron-receptive layer.

The detection sensitivity can be enhanced by adopting a concave-convex structure to increase the surface area of the electron-receptive layer 66 and thus to immobilize a larger amount of probe molecules. Since the size of biomolecules is about 0.1 to 20 nm, the diameter of pores formed by the concave-convex structure is preferably not less than 20 nm and not more than 150 nm. When the size of spaces formed by the concave-convex structure is smaller than the above size, the specific surface area is increased. In this case, however, the biomolecules cannot be bound to the probe, and, thus, the detection signal is lowered. When the concaves and convexes are coarse, the surface area is not increased very much and, thus, the signal intensity is not increased very much. The size of pores suitable for sensing of biomolecules is more preferably not less than 50 nm and not more than 150 nm.

In a preferred embodiment of the present invention, the adoption of a pillar structure of nano-scale pillars regularly arranged on the surface of the structure is preferred as the convex structure. The pillar structure can be produced by various conventional methods. A general method for forming the pillar structure is to use an anodized alumina having nano-scale pores as a mold. Examples of such methods include a method that comprises filling a ceramic sol into a mold, heat-treating the sol, and then removing the alumina mold by etching and a method that comprises providing a mold with a ceramic sol filled thereunto, removing the molded sol from the mold, and then heat-treating the molded sol. Methods for producing the pillar nanostructure include a method disclosed in JP 2004-130171A that comprises producing a nanostructure on a transparent electroconductive layer provided on a transparent base. Here a method is adopted that comprises filling a titania sol into a mold of an anodized alumina oxide, heat treating the sol at a temperature of 300 to 400° C., and then removing the mold by etching. As a result, titania nanotubes or nanowires are formed as the nanostructure.

In a preferred embodiment of the present invention, pores formed by firing an inorganic-organic hybrid precursor containing a ceramic component to oxidatively decompose organic matter and thus to form a gas phase are adopted as the concave structure. In the inorganic-organic hybrid precursor, for example, a metal-oxygen network structure formed by oxidation of an organometal compound (metal alkoxide) and a subsequent polycondensation reaction and an organic polymer are copresent. A method may also be adopted in which, for example, an organic polymer is added to commercially available titanium oxide particles (for example, anatase form of crystals manufactured by Tayka corporation, tradename AMT-600 (average particle diameter 30 nm)) or a titanium oxide dispersion. Various proposals have been made on compositions thereof. For example, JP H10 (1998)-212120A proposes a composition prepared by dispersing titanium oxide particles in a grime solvent (HO—(—CH$_2$CH$_2$O—)$_n$—R wherein n is 1 to 10; and R represents an alkyl or aryl group) and further adding an organic polymer as a dispersion aid. A specific surface area of 40 to 50 cm$^2$ per cm$^2$ (thickness 1 μm) can be provided by coating the dispersion having the composition onto a support by a suitable method (for example, dip coating, spray coating, spinner coating, blade coating, roller coating, wiper bar coating, or reverse roll coating) and firing the coating at 200 to 800° C. Further, JP 2001-233615A provides a fine three-dimensional concave structure by dropping a sol solution composed of tetraalkoxy titanium, a block copolymer of ethylene oxide, propylene oxide, and ethylene oxide, a stabilizer, and a solvent on a substrate, rotating the substrate at a high speed to vaporize the solvent and thus to form gel, and sintering the organic-inorganic composite titania thin film having a three-dimensional structure thus obtained at a high temperature to remove the block copolymer. Further, a method using oligosaccharide (trehalose) as the organic polymer is also disclosed (JP 2004-83376A). According to this method, a porous ceramic film having a porosity of 38 to 56% is obtained.

Thus, various proposals have been made on the method for regulating the fine concave-convex structure of the ceramic, and an electrode material having a large specific surface area can be developed by applying these methods to ceramic electrode materials suitable for the present technique.

In a preferred embodiment of the present invention, the working electrode further comprises an electroconductive base material, and the electron-receptive layer is provided on the electroconductive base material. The electroconductive base material usable in the present invention may be such that a support per se is electroconductive, for example, metals such as titanium. Further, the electroconductive base material may comprise an electroconductive material layer provided on a surface of a glass or plastic support. When an electroconductive base material having the electroconductive material layer is used, the electron-receptive layer is provided on the electroconductive material layer. Examples of electroconductive materials constituting the electroconductive material layer include metals such as platinum, gold, silver, copper, aluminum, rhodium, and indium; electroconductive ceramics such as carbon, carbides, and nitrides; and electroconductive metal oxides such as indium-tin composite oxide, fluorine-doped tin oxide, antimony-doped tin oxide, gallium-doped zinc oxide, or aluminum-doped zinc oxide. More preferred are indium-tin composite oxides (ITO) and metal oxides of fluorine-doped tin oxide (FTO). As described above, the electron-receptive layer per se can function also as an electroconductive base material, the electroconductive base material can be omitted. In the present invention, any electroconductive base material can be used without limitation as long as the material is electroconductive. Accordingly, the electroconductive base material includes a thin film-shaped or spot-shaped electroconductive material layer that as such does not have a satisfactory strength as a support.

In a preferred embodiment of the present invention, the electroconductive base material is substantially transparent, specifically has a light transmittance of not less than 10%, more preferably not less than 50%, still more preferably not less than 70%. According to this embodiment, a cell can be constructed so that light is applied from the backside (that is, the electroconductive base material) of the working electrode and light passed through the working electrode (that is, the electroconductive base material and the electron-receptive layer) excites the sensitizing dye. In a preferred embodiment of the present invention, the thickness of the electroconductive material layer is about 0.02 to 10 μm. Further, in a preferred embodiment of the present invention, the electroconductive base material has a surface resistivity of not more than 100 Ω/cm$^2$, more preferably not more than 40 Ω/cm$^2$. The lower limit of the surface resistivity of the electroconductive base material is not particularly limited. In general, however, the surface resistivity of the electroconductive base material would be about 0.1 Ω/cm$^2$.

Examples of preferred methods for forming the electron-receptive layer on the electroconductive base material include a method in which a dispersion or a colloidal solution of an electron receiving substance is coated on an electroconductive support, a method in which a precursor of fine semiconductor particles is coated on an electroconductive support and the precursor is then hydrolyzed by moisture in the air to obtain a finely particulate film (sol-gel method), a sputtering method, a CVD method, a PVD method, and a vapor deposition method. Methods for preparing a dispersion of fine semiconductor particles as the electron receiving substance include, in addition to the sol-gel method, a method in which the semiconductor is ground in a mortar, a method in which the semiconductor is dispersed while grinding in a mill, or a method in which, in synthesizing the semiconductor, the semiconductor is precipitated as fine particles in a solvent and, in this state, is used. Dispersion media used in this case include water or various organic solvents (for example, methanol, ethanol, isopropyl alcohol, dichloromethane, acetone, acetonitrile, or ethyl acetate). In the dispersion, if necessary, polymers, surfactants, acids, chelating agents and the like may be used as the dispersion aid.

Examples of preferred methods for coating a dispersion or a colloidal solution of the electron receiving substance include application methods such as roller coating and dip coating, metering methods such as air knife coating and blade coating, methods in which application and metering can be carried out in an identical part, for example, a wire bar method disclosed in JP S58 (1983)-4589A, and a slide hopper method, an extrusion method, a curtain method, a spin method, and a spray method described, for example, in U.S. Pat. Nos. 2,681,294, 2,761,419, and 2,761,791.

In a preferred embodiment of the present invention, when the electron-receptive layer is formed of fine semiconductor particles, the thickness of the electron-receptive layer is 0.1 to 200 μm, more preferably 0.1 to 100 μm, still more preferably 1 to 30 μm, most preferably 2 to 25 μm. According to this embodiment, the amount of the probe substance and the immobilized sensitizing dye per unit projected area can be increased to increase the amount of photocurrent and, further, the loss of electrons generated by recombination of charges can be reduced. The coverage of the fine semiconductor particles per $m^2$ of the electroconductive base material is preferably 0.5 to 400 g, more preferably 5 to 100 g.

In a preferred embodiment of the present invention, when the electron receiving substance comprises indium-tin composite oxide (ITO) or metal oxide of fluorine-doped tin oxide (FTO), the thickness of the electron-receptive layer is not less than 1 nm, more preferably 10 nm to 1 μm.

In a preferred embodiment of the present invention, coating of fine semiconductor particles on the electroconductive base material followed by heat treatment is preferred. According to this preferred embodiment, particles can be brought to electrical contact with each other, and, at the same time, an improvement in coating film strength and an improvement in adhesion to the support can be realized. The heat treatment temperature is preferably 40 to 700° C., more preferably 100 to 600° C. The heat treatment time is preferably approximately 10 min to 10 hr.

In a preferred embodiment of the present invention, when an electroconductive base material having a low melting point or softening point such as a polymer film is used, the formation of the film by a method not using high-temperature treatment is preferred from the viewpoint of preventing a heat deterioration. Examples of such film formation methods include pressing, low-temperature heating, electron-beam irradiation, microwave irradiation, electrophoresis, sputtering, CVD, PVD, and vapor deposition.

A probe substance is supported on the surface of the electron-receptive layer in the working electrode thus prepared. The probe substance may be supported on the working electrode by known methods. In a preferred embodiment of the present invention, when a single stranded nucleic acid is used as a probe substance, a method may be adopted in which an oxidized layer is formed on a surface of the working electrode and a nucleic acid probe and a working electrode are then bound through the oxidized layer. At that time, the nucleic acid probe can be immobilized on the working electrode by introducing a functional group into the end of the nucleic acid. According to this embodiment, the nucleic acid probe with the functional group introduced thereunto as such can be immobilized on the carrier by an immobilization reaction. The functional group may be introduced into the end of the nucleic acid by an enzyme reaction or with a DNA synthesizer. Enzymes usable in the enzyme reactions include, for example, terminal deoxynucleotidyl transferase, poly A polymerase, polynucleotide kinase, DNA polymerase, polynucleotide adenyl transferase, and RNA ligase. Further, the functional group may also be introduced by a polymerase chain reaction (PCR method), nick translation, or a random primer method. The functional group may be introduced into any part of the nucleic acid, that is, may be introduced into 3' end, 5' end or a random position.

In a preferred embodiment of the present invention, for example, amine, carboxylic acid, sulfonic acid, thiol, hydroxyl, and phosphoric acid are suitable for use as a functional group for immobilization on the working electrode of the nucleic acid probe. Further, in a preferred embodiment of the present invention, a material that forms a bridge between the working electrode and the nucleic acid probe may also be used for strongly immobilizing the nucleic acid probe on the working electrode. Examples of preferred crosslinking materials include silane coupling agents, titanate coupling agents, and electroconductive polymers such as polythiophene, polyacetylene, polypyrrole, and polyaniline.

In a preferred embodiment of the present invention, the immobilization of the nucleic acid probe can be efficiently carried out by a simpler procedure called physical adsorption. The nucleic acid probe can be physically adsorbed on the surface of the electrode, for example, as follows. At the outset, the surface of the electrode is cleaned with distilled water and alcohol using an ultrasonic cleaner. Thereafter, the electrode is inserted into a buffer solution containing a nucleic acid probe to allow the nucleic acid probe to be adsorbed on the surface of the carrier.

Nonspecific adsorption can be suppressed by adding a blocking agent after the adsorption of the nucleic acid probe. The blocking agent usable herein is not limited as long as a substance can fill up sites on the surface of the electron-receptive layer with the nucleic acid probe not adsorbed thereon and can be adsorbed on the electron receiving substance, for example, by chemical adsorption or physical adsorption. Preferably, the blocking agent is a substance that contains a functional group adsorbable through a chemical bond. Examples of preferred blocking agents, for example, in the case where titanium oxide is used as the electron-receptive layer include substances that contain functional groups adsorbable on titanium oxide, for example, carboxylic acid, phosphoric acid, sulfonic acid, hydroxyl, amino, pyridyl, and amide groups.

In a preferred embodiment of the present invention, a probe substance is supported on a plurality of areas separated from each other on the working electrode, and the areas are individually irradiated with light from the light source. According to this preferred embodiment, a plurality of samples can be measured on a piece of working electrode, and, thus, integration of DNA chips and the like is possible. In a more preferred embodiment of the present invention, a plurality of areas on which a probe substance is supported on the working electrode and which are separated from each other are patterned. In this case, preferably, while scanning light applied from the light source, for samples in the areas, the detection or quantitative determination of analytes are continuously carried out in single operation.

In a more preferred embodiment of the present invention, a plurality of kinds of probe substances may be supported on each of a plurality of areas, on the working electrode, that are separated from each other. According to this preferred embodiment, a number of samples, that is, samples of which the number is obtained by multiplying the number of areas by the number of kinds of probe substances for respective areas can be simultaneously measured.

In a more preferred embodiment of the present invention, different probe substances can be supported on a plurality of respective areas separated from each other on the working electrode. According to this preferred embodiment, probe substances, of which the number corresponds to the number of segmented areas, can be supported, and, thus, a number of kinds of analytes can be simultaneously measured.

Counter Electrode

The counter electrode used in the present invention is not particularly limited as long as current can flow across the counter electrode and the working electrode when the counter electrode has been brought into contact with the electrolyte medium. A counter electrode obtained by vapor-depositing a metal or an electroconductive oxide on an insulating support such as glass, plastic, or ceramic can be used. Further, the counter electrode may be prepared by forming a metallic thin film having a thickness of not more than 5 μm, preferably in the range of 3 nm to 3 μm, by vapor deposition or sputtering or the like. Examples of preferred materials usable in the counter electrode include platinum, gold, palladium, nickel, carbon, electroconductive polymers such as polythiophene, and electroconductive ceramics such as oxides, carbides, and nitrides. Platinum and carbon are more preferred, and platinum is most preferred. A thin film can be formed from these materials in the same manner as in electron-receptive layer formation.

EXAMPLES

A monobasic polymorph of a p53 gene was detected using the apparatus and method according to the present invention. A perfect match probe, a monobasic variant chain probe, and a perfect mismatch probe were immobilized on a working electrode side. The base sequences were as follows.

Perfect match (PM) probe: 5'-AGGATGGGCCTCAGGTTCATGCCGC-3' (SEQ ID No. 1)

Monobasic variant chain (SNP) probe: 5'-AGGATGGGCTCCGGTTCATGCCGC-3' (SEQ ID No. 2)

Perfect mismatch (MM) probe: 5'-GCGGCATGAACCGGAGGCCCATCCT-3' (SEQ ID No. 3)

Target DNA to be hybridized with these probes had the following base sequence.

```
                                              (SEQ ID No. 4)
Target DNA: 5'-Cy3-GCGGCATGAACCTGAGGCCCATCCT-3'
```

A fluorine-doped tin oxide (F—SnO$_2$:FTO) coated glass (manufactured by Al Special Glass Company, U film, sheet resistance: 12Ω/□, and shape: 75 mm×26 mm) was provided as a glass base material for a working electrode. This glass base material was ultrasonically cleaned in acetone for 15 min and subsequently in ultrapure water for 15 min to remove contaminants and residual organic matter. The glass base material was shaken in a 5 M aqueous sodium hydroxide solution for 15 min. Thereafter, shaking of the glass base material in ultrapure water for 5 min was repeated three times while replacing water with fresh water for each shaking to remove sodium hydroxide. The glass base material was taken out, and air was blown against the glass base material to blow away the residual water. The glass base material was then immersed in anhydrous methanol for dehydration.

3-Aminopropyltrimethoxysilane (APTMS) was added to a solvent composed of 95% methanol and 5% ultrapure water to bring the APTMS concentration to 0.2% by volume, and the mixture was stirred at room temperature for 5 min to prepare a solution for coupling treatment. The above glass base material was immersed in the solution for coupling treatment, and was then slowly shaken for 15 min. The glass base material was then taken out and was shaken in methanol for 3 min to remove excess solution for coupling treatment. This procedure was repeated three times while replacing methanol with fresh methanol for each time. Thereafter, the glass base material was held at 110° C. for 30 min to bind the coupling agent to the glass base material. The glass base material was cooled at room temperature, followed by adjustment to 10 μM. The glass base material was then held at 95° C. for 10 min and was then immediately transferred on ice. The perfect match chain, monobasic variant chain, and perfect mismatch probe DNAs (25 mer) that had been held for 10 min to denature DNA were spotted by three spots with MICROARRAYER (LT-BA manufactured by Filgen, spot pin diameter=1.5 mm) so that the central clearance of spots was 5 mm, followed by holding at 95° C. for 3 min to evaporate the solvent. Ultraviolet light was applied at 120 mJ with a UV cross linker (model CL-1000, manufactured by UVP corporation) to immobilize probe DNAs onto the glass base material. The glass base material was then shaken in a 0.2% SDS solution three times each for 5 min and was shaken in ultrapure water three times each for 5 min. The glass base material was immersed in boiling water for 2 min and was taken out. Air was blown against the glass base materials to blow away the residual water. Subsequently, the glass base material was immersed in absolute ethanol at 4° C. for one min for dehydration, and air was blown against the glass base materials to blow away the residual ethanol. Thus, a working electrode with probe DNAs immobilized thereonto was obtained. Further, a target DNA was adjusted to a concentration of 100 nM with a 2% NaCl-0.05% SDS solution, and the solution was then held at 95° C. for 10 min. The treated solution (130 μl) was fed into an automatic hybridization apparatus (Hyb-4, manufactured by Genomic Solutions) in which the probe-immobilized electrode was installed. In the automatic hybridization apparatus, the target DNA was hybridized at 45° C. for 3 min. The electrode was then washed with a 2×SSC-0.2% SDS solution at 28° C. for 3 min and was further washed with water at 28° C. for one min. Thus, a working electrode for current detection was obtained.

Figure 24:
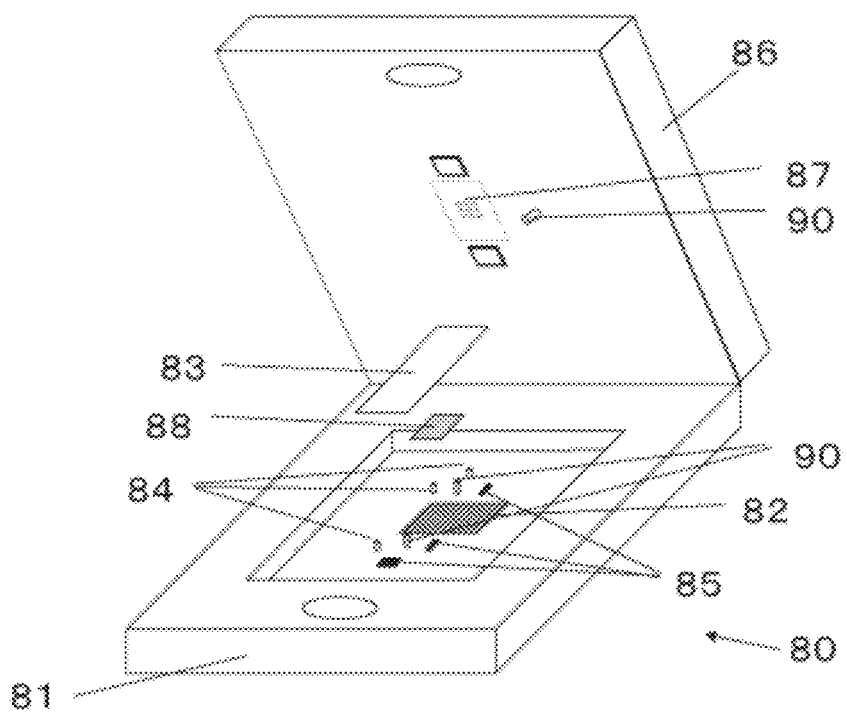
FIG. 24 is an exploded perspective view of a sensor unit in a measuring apparatus used in a working example.
Figure 25:
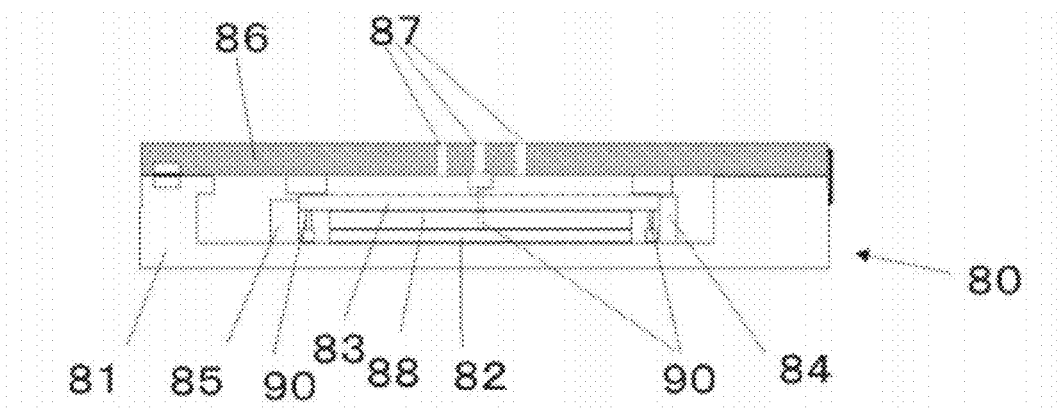
FIG. 25 is a cross-sectional view of a sensor unit in a measuring apparatus used in a working example.

The working electrode was installed in a measuring apparatus having a construction shown in FIG. 5. FIG. 24 is an exploded perspective view of a sensor unit in the measuring apparatus used in this experiment, and FIG. 25 is a cross-sectional view of the sensor unit. A sensor unit 80 comprises a counter electrode 82, a contact probe 90 that is electrically connected to a working electrode 83, a positioning pin 84 for positioning of the working electrode 83, an energizing member 85 provided to press the working electrode 83 against the positioning pin 84, an opening 87 for the application of light to detection spots, and a contact probe 90 that is electrically connected to the counter electrode 82. The electrolyte-containing sheet 88 was mounted on the counter electrode 82, and the working electrode 83 was installed so that the surface of the working electrode 83 was brought into contact with the electrolyte-containing sheet 88 along the positioning pin 84. Thereafter, an upper member 86 was superimposed on a lower member 81. Tetrapropyl ammonium iodide ($NPr_4I$) was provided (concentration 0.4 M) as an electrolyte in the electrolyte-containing sheet 88. Tetrapropyl ammonium iodide ($NPr_4I$) was dissolved in water to prepare an electrolysis solution. A 0.9 mm-thick filter paper cut unto a size of 26 mm×20 mm was immersed in the electrolysis solution and was then lightly dewatered to obtain the electrolyte-containing sheet 88.

Probe DNA-immobilized spots on the working electrode were successively irradiated each for 3 sec with light from a light source (wavelength: 532 nm, beam diameter: about 0.2 mm, output: 50 mW) mounted on an XY stage located above the sensor unit 80, and photocurrent observed in each spot irradiation was recorded. In the measurement in this experiment, before photocurrent detection, charged current produced in the formation of the sensor unit was discharged by connecting the sensor unit to a discharge circuit after the connection of the sensor unit to the ammeter. Further, before the measurement of photocurrent values of respective detection spots, the XY stage was regulated so that the application of light from the light source was stopped for one sec at a position between an opening of the sensor unit corresponding to a detection spot as a measurement object and an opening corresponding to a detection spot subjected to the latest measurement, and the sensor unit was connected to the discharge circuit, current derived from the detection spot subjected to the latest measurement was discharged and the XY stage was then moved to the detection spot as the measurement object. A current value observed between both the openings (that is, a current value in such a state that the working electrode was not irradiated with light due to light blocking) was regarded as a base current value, and a difference between a photocurrent value derived from each spot and a base current value obtained by the latest measurement was regarded as an observed value.

Figure 26:
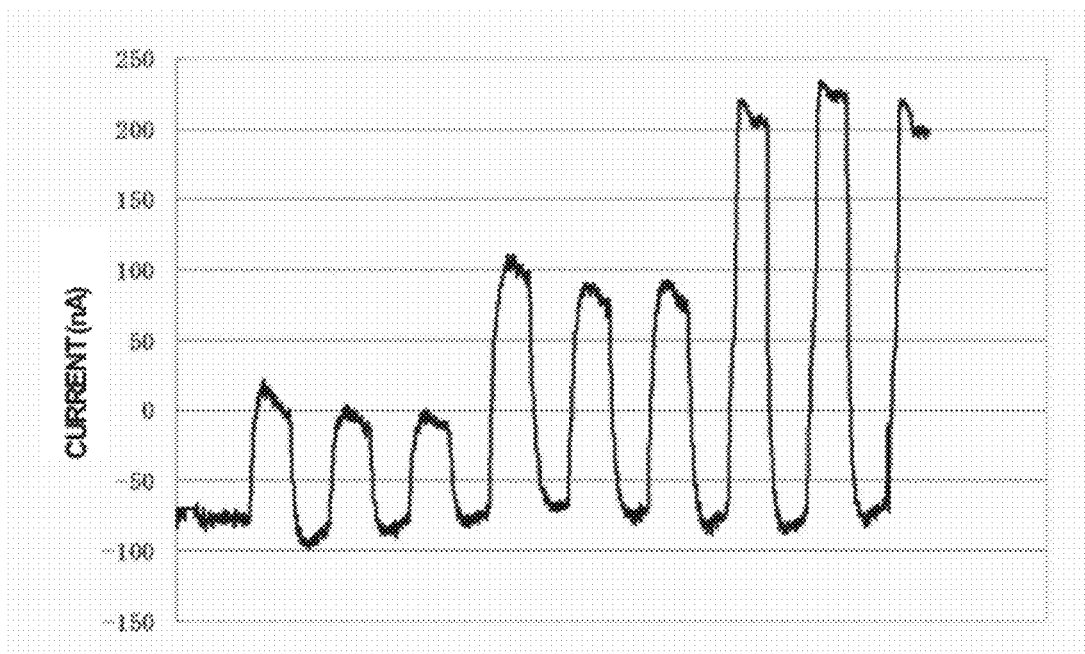
FIG. 26 is a diagram showing a change in photocurrent obtained in irradiation of each detection spot with light obtained in a working example.
Figure 27:
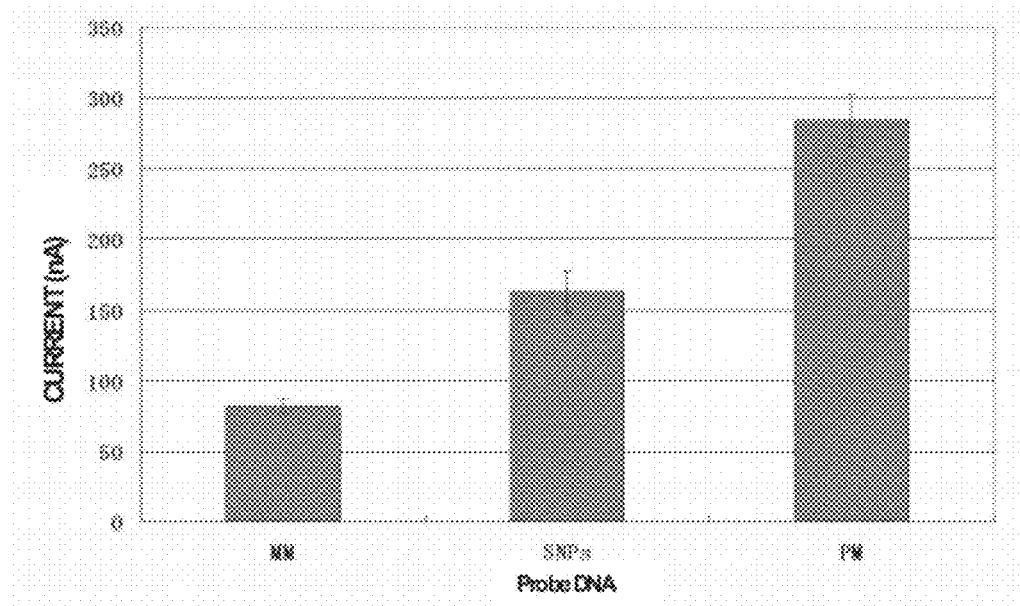
FIG. 27 is a graph of a difference, between each detection spot-derived current and base current that were obtained in a working example, organized for each probe DNA, in terms of average and standard deviation (error bar: ±1 SD).

FIG. 26 shows a current waveform thus obtained, and FIG. 27 shows the summarized results (N=3) of a difference between a photocurrent value derived from each spot and a base current value just before the measurement of the measurement object spot for each probe DNA. The photocurrent value derived from each spot and the base current value each were calculated as an average of five points at each central part. As can be seen from the current waveform shown in FIG. 26, charged current at an early stage of photocurrent detection was suppressed, and the photocurrent value derived from a detection spot subjected to the latest measurement could be refreshed. Therefore, as is apparent from FIG. 27, a difference of one base (a difference in current value between PM and SNPs) could be distinguished statistically significantly.

The invention claimed is:

1. A measuring apparatus for specifically detecting an analyte using photocurrent generated by photoexcitation of a sensitizing dye, comprising:
   a sensor unit comprising a working electrode, a counter electrode, and an electrolyte-containing substance,
   a single or plurality of light sources that apply light to the working electrode;
   an ammeter that measures current which flows across the working electrode and the counter electrode;
   a discharge device that discharges charged current and photocurrent derived from a detection spot subjected to the latest photocurrent measurement; and
   a switching device that connects the sensor unit to the ammeter or the discharge device,
   wherein the specific detection of the analyte is carried out while controlling timing of light irradiation and timing of connection of the sensor unit to the ammeter and the discharge device.

2. The measuring apparatus according to claim 1, which is controlled so that, when the working electrode and the counter electrode is brought into contact with the electrolyte-containing substance, the sensor unit is connected to the discharge device to discharge charged current generated in the formation of the sensor unit,
   after the discharge of the charged current, the sensor unit is connected to the ammeter and a single or plurality of detection spots formed on the working electrode are successively irradiated with light to detect photocurrent derived from the sensitizing dye bound to the detection spot.

3. The measuring apparatus according to claim 1, which is controlled so that, in the detection of photocurrent in a plurality of detection spots, after the detection of photocurrent in one detection spot, the sensor unit is connected to the discharge device to discharge photocurrent derived from the detection spot subjected to the latest photocurrent measurement, and the sensor unit is again connected to the ammeter, followed by irradiation of the detection spot with light to detect photocurrent derived from the sensitizing dye bound to the detection spot.

4. The measuring apparatus according to claim 1, wherein the electrolyte-containing substance is an electrolysis solution,
   the sensor unit comprises: a flow passage provided so that the electrolysis solution flows therethrough and the electrolysis solution comes into contact with the working electrode and the counter electrode; and further
   a pump that feeds the electrolysis solution into the flow passage in the sensor unit.

5. The measuring apparatus according to claim 4, which further comprises a valve that controls the feed of the electrolysis solution.

6. The measuring apparatus according to claim 1, which further comprises an XY moving device that moves the light source relatively in an XY direction relative to the working electrode.

7. The measuring apparatus according to claim 6, which further comprises a computer that controls through an interface board the ammeter, the light source, the XY moving device, the discharge device, and the switching device and that receives through an interface board current signals from the ammeter.

8. The measuring apparatus according to claim 7, wherein the computer comprises a control computation means that determines at least one of the presence of the analyte, the type, and the concentration based on the electric signals.

9. The measuring apparatus according to claim 1, which is used for specifically detecting an analyte using photocurrent that flows across a working electrode and a counter electrode attributable to electron transfer from a photoexcited sensitizing dye to the working electrode, wherein
   the working electrode has a single or a plurality of detection spots with a probe substance specifically bindable directly or indirectly to the analyte being supported on a surface thereof,
   a sample solution containing the analyte and the sensitizing dye are brought into contact with the surface of the working electrode to immobilize the sensitizing dye on the working electrode through the specific bond, and
   the measuring apparatus is controlled so that the working electrode and the counter electrode are brought into contact with the electrolyte-containing substance to form a sensor unit;
   the sensor unit formed by bringing the working electrode and the counter electrode into contact with the electrolyte-containing substance is connected to a discharge device; charged current generated in the formation of the sensor unit is discharged before the start of current detection; after the discharge of the charged current, the sensor unit is connected to an ammeter; the single or plurality of detection spots provided on the working electrode are successively irradiated with light; and photocurrent derived from the dye bound to each of the detection spots is detected.

10. The measuring apparatus according to claim 1 which is used for specifically detecting an analyte using photocurrent that flows across a working electrode and a counter electrode attributable to electron transfer from a photoexcited sensitizing dye to the working electrode, wherein
    the working electrode has a single or a plurality of detection spots with a probe substance specifically bindable directly or indirectly to the analyte being supported on a surface thereof, and
    a sample solution containing the analyte and the sensitizing dye are brought into contact with the surface of the working electrode to immobilize the sensitizing dye to the working electrode through the specific bond, and
    the measuring apparatus is controlled by a step of discharging, before the start of photocurrent detection, charged current generated in the formation of the sensor unit and a step of, after the discharge of the charged current, connecting the sensor unit to an ammeter, connecting the sensor unit to the discharge device before the photocurrent detection of each of the detection spots, discharging photocurrent derived from a detection spot subjected to the latest measurement of photocurrent detection, then again connecting the sensor unit to the ammeter, irradiating a detection spot as a measurement object with light, and detecting photocurrent derived from the dye bound to the detection spot, whereby specific detection can be realized in a plurality of detection spots.

11. A sensor unit that is used for a measuring apparatus according to claim 4 and specifically detects an analyte using photocurrent that flows across a working electrode and a counter electrode attributable to electron transfer from a photoexcited sensitizing dye to the working electrode, wherein the sensor unit comprises a working electrode and a counter electrode and further comprises a flow passage that allows an electrolysis solution, a wash solution, and a reaction solution to be stored therein and to flow therethrough so as to come into contact with the working electrode and the counter electrode.

12. A sensor unit that is used for a measuring apparatus according to claim 4 and specifically detects an analyte using photocurrent that flows across a working electrode and a counter electrode attributable to electron transfer from a photoexcited sensitizing dye to the working electrode, wherein the sensor unit comprises an electrode unit comprising coplanarily patterned working electrode and counter electrode, and the sensor unit further comprises a flow passage that allows an electrolysis solution, a wash solution, and a reaction solution to be stored therein and to flow therethrough so as to come into contact with the working electrode and the counter electrode.

13. The measuring apparatus according to claim 6, which further comprises a computer that controls through an interface board the ammeter, the light source, the XY moving device, the discharge device, the switching device, and the pump and that receives through an interface board current signals from the ammeter.

14. The measuring apparatus according to claim 13, wherein the computer comprises a control computation means that determines at least one of the presence of the analyte, the type, and the concentration based on the electric signals.

15. The measuring apparatus according to claim 6, which further comprises a computer that controls through an interface board the ammeter, the light source, the XY moving device, the discharge device, the switching device, the pump, and the valve and that receives through an interface board current signals from the ammeter.

16. The measuring apparatus according to claim 15, wherein the computer comprises a control computation means that determines at least one of the presence of the analyte, the type, and the concentration based on the electric signals.

17. The measuring apparatus according to claim 9, wherein the analyte is bound to the probe substance by bringing the sample solution containing the analyte into contact with the working electrode in the copresence of a sensitizing dye, and the sample solution further contains a mediating substance that is previously labeled with a sensitizing dye and is bindable specifically to the analyte, and a bound product between the mediating substance and the analyte is bound specifically to the probe substance.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial
<220> FEATURE:
<223> OTHER INFORMATION: probe (PM)

<400> SEQUENCE: 1
aggatgggcc tcaggttcat gccgc                                       25

<210> SEQ ID NO 2
<211> LENGTH: 25
<212> TYPE: DNA
<213> ORGANISM: Artificial
<220> FEATURE:
<223> OTHER INFORMATION: probe (SNP)

<400> SEQUENCE: 2
aggatgggcc tccggttcat gccgc                                       25

<210> SEQ ID NO 3
<211> LENGTH: 25
<212> TYPE: DNA
<213> ORGANISM: Artificial
<220> FEATURE:
<223> OTHER INFORMATION: probe (MM)

<400> SEQUENCE: 3
gcggcatgaa ccggaggccc atcct                                       25

<210> SEQ ID NO 4
<211> LENGTH: 25
<212> TYPE: DNA
<213> ORGANISM: Artificial
<220> FEATURE:
```

```
<223> OTHER INFORMATION: target

<400> SEQUENCE: 4
gcggcatgaa cctgaggccc atcct                                            25
```